(12) United States Patent
Kohr et al.

(10) Patent No.: US 9,290,688 B2
(45) Date of Patent: *Mar. 22, 2016

(54) ALKALINE MICROBIAL ENHANCED OIL RECOVERY

(75) Inventors: William J. Kohr, Davis, CA (US); Zhaoduo Zhang, Pleasanton, CA (US); David J. Galgoczy, San Francisco, CA (US)

(73) Assignee: GEO FOSSIL FUELS, LLC, Golden, CO (US)

( * ) Notice: Subject to any disclaimer, the term of this patent is extended or adjusted under 35 U.S.C. 154(b) by 581 days.

This patent is subject to a terminal disclaimer.

(21) Appl. No.: 13/385,520

(22) Filed: Feb. 23, 2012

(65) Prior Publication Data

US 2013/0062053 A1 Mar. 14, 2013

Related U.S. Application Data

(60) Provisional application No. 61/446,674, filed on Feb. 25, 2011, provisional application No. 61/496,461, filed on Jun. 13, 2011, provisional application No. 61/633,785, filed on Feb. 17, 2012.

(51) Int. Cl.
*C09K 8/582* (2006.01)
*C12N 1/26* (2006.01)
*C12N 9/02* (2006.01)

(52) U.S. Cl.
CPC . *C09K 8/582* (2013.01); *C12N 1/26* (2013.01); *C12N 9/0077* (2013.01); *C12Y 114/15003* (2013.01)

(58) Field of Classification Search
None
See application file for complete search history.

(56) References Cited

U.S. PATENT DOCUMENTS

| | | | | |
|---|---|---|---|---|
| 2,413,278 A | * | 12/1946 | Zobell | 166/264 |
| 5,013,654 A | | 5/1991 | Banerjee et al. | |
| 5,037,758 A | | 8/1991 | Mulligan et al. | |
| 5,297,625 A | * | 3/1994 | Premuzic et al. | 166/246 |
| 6,022,834 A | | 2/2000 | Hsu et al. | |
| 6,589,772 B1 | * | 7/2003 | Banfield et al. | 435/243 |
| 7,070,944 B2 | | 7/2006 | Black et al. | |
| 7,975,762 B2 | * | 7/2011 | Pfeiffer et al. | 166/246 |
| 8,316,933 B2 | * | 11/2012 | Kohr | 166/246 |
| 2009/0082227 A1 | * | 3/2009 | Hnatow et al. | 507/201 |
| 2011/0067856 A1 | | 3/2011 | Kohr | |

OTHER PUBLICATIONS

International Search Report mailed Jul. 6, 2012 for related PCT Patent Application No. PCT/US2012/026395.
Pinzon-Martinez D L et al: "Thermophilic bacteria from Mexican thermal environments: isolation and potential applications", Environmental Technology, vol. 31, No. 8-9, Jul. 1, 2010, pp. 957-966.

(Continued)

*Primary Examiner* — Angela M DiTrani
(74) *Attorney, Agent, or Firm* — Ginger R. Dreger; Arnold & Porter LLP

(57) ABSTRACT

A method of enhanced oil recovery that includes water-flooding an oil reservoir with an alkaline fluid or a fluid containing a compound toxic to indigenous microbes and inoculating the oil reservoir with a consortium comprising microbes that naturally are, or are engineered to be, obligatory alkaliphilic, halo-alkaliphilic or alkaline tolerant, and naturally are, or are engineered to be, deficient in their ability to utilize short chain hydrocarbons of 12 carbons or less but have the ability to convert hydrocarbons into fatty acids.

26 Claims, 5 Drawing Sheets

(56) References Cited

OTHER PUBLICATIONS

Hao Ruixia et al: "Crude-oil-degrading thermophilic bacterium isolated from an oil field", Canadian Journal of Microbiology, vol. 50, No. 3, Mar. 1, 2004, pp. 175-182.

Kenzo Kubota et al: "Phylogenetic analysis of long-chain hydrocarbon-degrading bacteria and evaluation of their hydrocarbon-degradation by the 2,6-DCPIP assay", Biodegradation, vol. 19, No. 5, Feb. 19, 2008, pp. 749-757.

Lu Feng et al: "Genome and proteome of long-chain alkane degrading Geobacillus thermodenitrificans NG80-2 isolated from a deep-subsurface oil reservoir", Proceedings of the National Academy of Sciences, vol. 104, No. 13, Mar. 27, 2007, pp. 5602-5607.

Smits, Theodorus: "Cloning and functional analysis of bacterial genes involved in alkane oxidation", Dissertation for the degree of Doctor of Natural Sciences , 2001.

Geissdörfer et al: "The genes rubA and rubB for alkane degradation in Acinetobacter sp. strain ADP1 are in an operon with estB, encoding an esterase, and oxyR.", Journal of Bacteriology, vol. 181, No. 14, Jul. 1, 1999, pp. 4292-4298.

L. G. Whyte et al: "Gene Cloning and Characterization of Multiple Alkane Hydroxylase Systems in Rhodococcus Strains Q15 and NRRL B-16531", Applied and Environmental Microbiology, vol. 68, No. 12, Dec. 1, 2002, pp. 5933-5942.

Allers et al. "Development of additional selectable markers for the halophilic archaeon Haloferax volcanii based on the leuB and trpA genes", Applied Environ. Microbiol. 70: 943-953, 2004.

Al-Awadhi et al. "Alkaliphilic and halophilic hydrocarbon-utilizing bacteria from Kuwait coasts of the Arabian Gulf", Applied Microbiol. Biotechnol. 77(1):183-186 ,2007.

Bitan-Banin et al. "Development of a gene knockout system for the halophilic archaeon haloferax volcanii by use of the pyrE gene", J. Bacteriol. 185(3):772-778, 2003.

Cayol et al "Isolation and characterization of Halothermothrix orenii gen. nov., sp. Nov., a halophilic, thermophilic, fermentative, strictly anaerobic bacterium", Int. J. Syst. Bacteriol. 44(3): 534-540, Jul. 1994.

Cooper et al. "Enhanced production of surfactin from bacillus subtilis by continuous product removal and metal cation additions", Appl. Environ. Microbiol. 42(3):408-412, 1981.

Chuang et al. "Characterization of twenty-six new heat shock genes of *Escherichia coli*", J. Bacteriol. 175(16): 5242-5252, Aug. 1993.

Dinamarca et al. "Expression of the pseudomonas putida OCT plasmid alkane degradation pathway is modulated by two different gloval control signals: evidence from continuous cultures", J. Bacteriol. 185(16):4772-4778, Aug. 2003.

Enache et al. "Phylogenetic relationships within the family halobacteriaceae inferred from rpoB' gene and protein sequences", International Journal of Systematic and Evolutionary Microbiology 57(Pt 10): 2289-2295, 2007.

Feng et al. "Genome and proteome of long-chain alkane degrading geobacillus thermodenitrificans NG80-2 isolated from a deep-subsurface iuk reservoir", Proc Natl. Acad Sci. USA 104(13):5602-5607, Epub Mar. 19, 2007.

Fire et al. "Potent and specific genetic interference by double-stranded RNA in caenorhabditis elegans", Nature 391:806-811, Feb. 19, 1998.

Guerra-Santos et al. "Dependence of pseudomonas aeruginosa continuous culture biosurfactant production on nutritional and environmental factors", Appl. Microbial. Biotech. 24:443-448, 1986.

Hao et al. "Crude-oil-degrading thermophillic bacterium isolated from an oil field", Can J. Microbiol. 50(3):175-182, Mar. 2004.

Horikoshi, K. "Alkaliphiles: some applications of their products for biotechnology", Microbiology Molecular Biology Review 63(4): 735-750, Dec. 1999.

Javaheri et al. "Anaerobic production of a biosurfactant by bacillus licheniformis JF-2", Appl. Environ. Microbiol. 50(3): 698-700, Sep. 1985.

Kaiser et al. "Microbial metabolism of pyridine, quinoline, acridine and their derivatives under aerobic and anaerobic conditions", Microbiological Reviews 60 (3):483-498, Sep. 1996.

Kubota et al. "Phylogenetic analysis of long-chain hydrocarbon-degrading bacteria and evaluation of their hydrocarbon-degradation by the 2,6-DCPIP assay", Biodegradation 19(5):749-757, 2008.

Gray et al. "Molecular mechanisms of biocatalytic desulfurization of fossil fuels", Nature Biotechnology 14(13);1705-1709 , Dec. 1996.

Hirsch et al. "A family of fatty acid transporters conserved from mycobacterium to man", Proc. Natl. Acad. Sci. USA 95(15): 8625-8629, Jul. 21, 1998.

Geissdorfer et al. "The genes rubA and rubB for alkane degradation in acinetobacter sp. Strain ADP1 are in an operon with estB, encoding an esterase and oxyR", Journal Bacteriology 181(14):4292-4298,1999.

George et al. "A novel thermostable xylanase from thermomonospora sp.:influence of additives on thermostability", Bioresource Technology 78(3):221-224, Jul. 2001.

International Search Report received in corresponding application PCT/US2012/026395.

Lang et al. "Rhamnose lipids-biosynthesis, microbial production and application potential", Appl. Microbiol. Biotechnol. 51(1):22-32, 1999.

Makarova et al. "Comparative genomics of archaea: how much have we learned in six years, and what's next?", Genome Biology 4(8):115, Jul. 16, 2003.

Manilla-Perez et al. "Analysis of lipid export in hydrocarbonoclastic bacteria of the genus *Alcanivorax*: Identification of lipid export-negative mutants of alcanivorax borkumensis SK2 and alcanivorax jadensis T9", J. Bacteriology 192(3): 643-656 , Feb. 2010.

Minz et al. "Diversity of sulfate-reducing bacteria in oxic and anoxic regions of a microbial mat characterized by comparative analysis of dissimilatory sulfite reductase genes", Appl. Environ. Microbiol. 65(10): 4666-4671, Oct. 1999.

Nichols, NM. "Endonucleases", Current Protocols in Molecular Biology 3.12.1-3.12.7, Jan. 2011.

Pinzon-Martinez et al. "Thermophilic bacteria from Mexican thermal environments: isolation and potential applications", Environmental Technology 31: 957-966, 2010.

Purwasena et al. "Estimation of the potential of an oil-viscosity-reducing bacteria, petrotoga s.p., isolated from an oilfield for MEOR", International Petroleum Technology Conference 13861, Dec. 2009.

Raaka et al. "Inhibition of fatty acid oxidation by 2-bromooctanoate. Evidence for the enzymatic formation of 2-bromo-3-ketooctanoyl coenzyme A and the inhibition of 3-ketothiolase", J. Biological Chemistry 254(14): 6755-6762, Jul. 25, 1979.

Roadcap et al. "Extremely alkaline (ph > 12) ground water hosts diverse microbial community", Ground Water 44(4): 511-517, Jul.-Aug. 2006.

Sato et al "Cloning of genes involved in carbazole degradation of pseudomonas sp. Strain CA10: nucleotide sequences of genes and characterization of meta-cleavage enzymes and hydrolase", J. Bacteriol. 179(15): 4841-4849, Aug. 1997.

Santegoeds et al. "Structural and functional dynamics of sulfate-reducing populations in bacterial biofilms", Applied Environmental Microbiology 64(10):3731-3739 , Oct. 1998.

Schneiker et al. "Genome sequence of the ubiquitous hydrocarbon-degrading marine bacterium Alcanivorax borkumensis.", Nature Biotechnol. 24(8):997-1004, Aug. 2006.

Smits et al. "Cloning and functional analysis of bacterial genes involved in alkane oxidation", Dissertation for the degree of doctor of Natural Sciences, 2001.

Steen et al. "Microbial production of fatty-acid derived fuels and chemicals from plant biomass", Nature 463(7280): 559-562, Jan. 28, 2010.

Thijsse GJ "Fatty-acid accumulation by acrylate inhibition of beta-oxidation in alkane-oxidizing pseudomonas", Biochim. Biophys. Acta 84:195-197, Apr. 20, 1964.

Tindall et al "Validation of the publication of new names and new combinations previously effectively published outside the ILJSB", International Journal of Systematic Bacteriology , p. 355-357, Jul. 1984.

(56) References Cited

OTHER PUBLICATIONS

Tindall et al. "Natronobacterium gregoryi" (ATCC 43098).
Tindall et al. "Natrialba magadii" (ATCC 43099).
Shirai et al. "High-resolution crystal structureof M-protease: phylogeny aided analysis of the high-alkaline adaptation mechanism", Protein Engineering 10(6): 627-634, Jun. 1997.
Van Hamme, et al. "Recent advances in petroleum microbiology", Microbiology and Molecular Biology Reviews 67(4):503-549, Dec. 2003.
Whyte et al. "Gene cloning and characterization of multiple alkane hydroxylase systems in rhodococcus strains Q15 and NRRL B-16531", Applied and Environmental Microbiology 68(12):5933-5942, Dec. 2002.
Wu, Q. et al. "FATP1 is an insulin-sensitive fatty acid transporter involved in diet-induced obesity", Mol. Cell Biol. 26(9):3455-3467, May 2006.
Zhao et al. "Production of D-(-)-3-hydroxyalkanoic acid by recombinant *Escherichia coli*", FEMS Microbiology Letters 218 (1):59-64, Jan. 21, 2003.

* cited by examiner

Fatty acid of n+2 carbons    Soap of n+2 carbons

FIGURE 4

SEQUENCE LISTING

<160> NUMBER OF SEQ ID NOS: 21

<210> SEQ ID NO 1
<211> LENGTH: 440
<212> TYPE: PRT
<213> ORGANISM: Geobacillus thermodenitrificans

<400> SEQUENCE: 1

Met Thr Lys Lys Ile His Ile Asn Ala Phe Glu Met Asn Cys Val Gly
1               5                   10                  15

His Ile Ala His Gly Leu Trp Arg His Pro Glu Asn Gln Arg His Arg
            20                  25                  30

Tyr Thr Asp Leu Asn Tyr Trp Thr Glu Leu Ala Gln Leu Leu Glu Lys
        35                  40                  45

Gly Lys Phe Asp Ala Leu Phe Leu Ala Asp Val Val Gly Ile Tyr Asp
    50                  55                  60

Val Tyr Arg Gln Ser Arg Asp Thr Ala Val Arg Glu Ala Val Gln Ile
65                  70                  75                  80

```
Pro Val Asn Asp Pro Leu Met Leu Ile Ser Ala Met Ala Tyr Val Thr
                85                  90                  95

Lys His Leu Ala Phe Ala Val Thr Phe Ser Thr Thr Tyr Glu His Pro
            100                 105                 110

Tyr Gly His Ala Arg Arg Met Ser Thr Leu Asp His Leu Thr Lys Gly
        115                 120                 125

Arg Ile Ala Trp Asn Val Val Thr Ser His Leu Pro Ser Ala Asp Lys
    130                 135                 140

Asn Phe Gly Ile Lys Lys Ile Leu Glu His Asp Glu Arg Tyr Asp Leu
145                 150                 155                 160

Ala Asp Glu Tyr Leu Glu Val Cys Tyr Lys Leu Trp Glu Gly Ser Trp
                165                 170                 175

Glu Asp Asn Ala Val Ile Arg Asp Ile Glu Asn Asn Ile Tyr Thr Asp
            180                 185                 190

Pro Ser Lys Val His Glu Ile Asn His Ser Gly Lys Tyr Phe Glu Val
        195                 200                 205

Pro Gly Pro His Leu Cys Glu Pro Ser Pro Gln Arg Thr Pro Val Ile
    210                 215                 220

Tyr Gln Ala Gly Met Ser Glu Arg Gly Arg Glu Phe Ala Ala Lys His
225                 230                 235                 240

Ala Glu Cys Val Phe Leu Gly Gly Lys Asp Val Glu Thr Leu Lys Phe
                245                 250                 255

Phe Val Asp Asp Ile Arg Lys Arg Ala Lys Lys Tyr Gly Arg Asn Pro
            260                 265                 270

Asp His Ile Lys Met Phe Ala Gly Ile Cys Val Ile Val Gly Lys Thr
        275                 280                 285

His Asp Glu Ala Met Glu Lys Leu Asn Ser Phe Gln Lys Tyr Trp Ser
    290                 295                 300

Leu Glu Gly His Leu Ala His Tyr Gly Gly Gly Thr Gly Tyr Asp Leu
305                 310                 315                 320

Ser Lys Tyr Ser Ser Asn Asp Tyr Ile Gly Ser Ile Ser Val Gly Glu
                325                 330                 335

Ile Ile Asn Asn Met Ser Lys Leu Asp Gly Lys Trp Phe Lys Leu Ser
            340                 345                 350

Val Gly Thr Pro Lys Lys Val Ala Asp Glu Met Gln Tyr Leu Val Glu
        355                 360                 365

Glu Ala Gly Ile Asp Gly Phe Asn Leu Val Gln Tyr Val Ser Pro Gly
    370                 375                 380

Thr Phe Val Asp Phe Ile Glu Leu Val Val Pro Glu Leu Gln Lys Arg
385                 390                 395                 400

Gly Leu Tyr Arg Val Asp Tyr Glu Glu Gly Thr Tyr Arg Glu Lys Leu
                405                 410                 415

Phe Gly Lys Gly Asn Tyr Arg Leu Pro Asp Asp His Ile Ala Ala Arg
            420                 425                 430

Tyr Arg Asn Ile Ser Ser Asn Val
        435                 440

<210> SEQ ID NO 2
<211> LENGTH: 461
<212> TYPE: PRT
<213> ORGANISM: Halalkalicoccus jeotgali

<400> SEQUENCE: 2

Met Thr Asp Glu Arg Met Gly Leu Asn Leu Phe Thr Met Asn Ser Val
```

```
  1               5                    10                   15
Glu His Val Ser Ala Gly Ser Trp Arg Tyr Pro Gly Asp Gln Ser His
                20                  25                  30

Arg Tyr Thr Asp Arg Glu Tyr Trp Thr Glu Leu Ala Arg Thr Ala Glu
                35                  40                  45

Arg Gly Gly Phe Asp Ala Ile Phe Phe Ala Asp Val Arg Gly Ile Tyr
 50                      55                  60

Asp Val Tyr Asp Asp Gly Arg Glu Thr Ala Ile Glu Arg Ala Val Gln
 65                  70                  75                  80

Thr Pro Ser Asn His Pro Gln Ala Leu Val Pro Ala Met Ala Glu Val
                85                  90                  95

Thr Asp His Leu Gly Phe Ala Ile Thr Arg Ser Thr Thr Tyr Ala His
                100                 105                 110

Pro Tyr Gln Leu Ala Arg Glu Phe Ser Thr Leu Asp His Leu Thr Asp
                115                 120                 125

Gly Arg Val Ala Phe Asn Val Val Thr Ser Tyr Leu Asp Ser Ala Ala
 130                     135                 140

Arg Asn Leu Gly Leu Glu Gln Arg Met Asp His Asp Gly Arg Tyr Asp
145                  150                 155                 160

Arg Ala Ala Glu Phe Met Gln Val Cys Tyr Arg Leu Trp Glu Gly Ser
                165                 170                 175

Trp Asp Asp Asp Ala Val Ala Arg Asp Arg Glu Gln Gly Val Tyr Thr
                180                 185                 190

Asp Pro Glu Lys Val Arg Glu Ile Asp Phe Glu Gly Glu Tyr Phe Asp
                195                 200                 205

Val Gln Gly Pro His Gly Cys Glu Pro Ser Pro Gln Arg Thr Pro Val
 210                     215                 220

Ile Tyr Gln Ala Gly Ser Ser Glu Arg Gly Arg Glu Phe Ala Ala Lys
225                  230                 235                 240

Asn Ala Glu Ala Val Phe Thr Ser Gln Pro Thr Glu Lys Gly Val Arg
                245                 250                 255

Asp Tyr Met Ala Asp Met Arg Glu Arg Ala Ala Glu Cys Gly Arg Asp
                260                 265                 270

Pro Asp Ser Leu Asp Phe Phe Ala Gly Leu Val Pro Ile Val Gly Glu
                275                 280                 285

Thr Ala Glu Ile Ala Gln Ala Lys His Glu Ser Tyr Lys Glu Thr Ile
 290                     295                 300

Asp Val Glu Ala Thr Leu Ala Leu Leu Ser Gly Phe Met Asp Met Asp
305                  310                 315                 320

Leu Ser Glu Leu Asn Pro Asp Gln Lys Leu Glu His Ile Glu Thr Glu
                325                 330                 335

Ala Ile Gln Gly Ala Val Asn Ala Phe Thr Lys Ser Asp Pro Asp Arg
                340                 345                 350

Glu Trp Thr Val Arg Glu Met Ala Gln Phe Ala Gly Leu Gly Thr Thr
                355                 360                 365

Ser Pro Val Val Gly Pro Pro Glu Glu Ile Ala Asp Ala Phe Glu
 370                     375                 380

His Trp Phe His Glu Val Gly Val Asp Gly Phe Asn Val Lys Glu Val
385                  390                 395                 400

Ile Arg Pro Asn Ser Leu Arg Asp Phe Val Asp Leu Val Pro Glu
                405                 410                 415

Leu Arg Glu Arg Gly Leu Val Arg Gly Glu Tyr Glu Asp Gly Thr Leu
                420                 425                 430
```

```
Arg Glu Ser Leu Thr Gly Arg Ser Glu Leu Ala Glu Asp His Pro Gly
        435                 440                 445

Lys Arg Glu Ala Ile Ser Ala Met Gly Leu Arg Glu Leu
    450                 455                 460

<210> SEQ ID NO 3
<211> LENGTH: 458
<212> TYPE: PRT
<213> ORGANISM: Halorubrum lacusprofundi

<400> SEQUENCE: 3

Met Ser Asp His Leu His Leu Asn Leu Phe Thr Met Ala Ser Val Glu
1               5                   10                  15

His Val Ser Pro Gly Ser Trp Thr Tyr Pro Gly Asp Arg Ser Pro Glu
            20                  25                  30

Tyr Thr Asp Arg Glu Tyr Trp Thr Glu Val Ala Arg Thr Ala Glu Arg
        35                  40                  45

Gly Gly Phe Asp Ala Val Phe Ala Asp Val Arg Gly Ile Tyr Asp
    50                  55                  60

Val Tyr Gly Asp Arg Glu Thr Ala Val Glu Lys Ala Val Gln Thr
65                  70                  75                  80

Pro Ala Ser Asp Pro Gln Leu Val Val Pro Ala Met Ala Glu Val Thr
                85                  90                  95

Asp Asp Leu Gly Phe Ala Ile Thr Arg Ser Thr Thr Tyr Thr His Pro
            100                 105                 110

Tyr Gln Leu Ala Arg Glu Phe Ser Thr Leu Asp His Leu Thr Asp Gly
        115                 120                 125

Arg Val Ala Ile Asn Val Val Thr Ser Tyr Leu Gln Ser Ala Ala Glu
    130                 135                 140

Asn Leu Gly Leu Ser Glu Arg Met Asp Lys Gln Thr Arg Tyr Asp Arg
145                 150                 155                 160

Ala Asp Glu Phe Leu Asp Val Cys Tyr Lys Leu Trp Glu Glu Ser Trp
                165                 170                 175

Asp Asp Asp Ala Val Glu Ile Asp Arg Glu Ala Gly Arg Tyr Thr Asp
            180                 185                 190

Pro Glu Lys Val Ser Thr Ile Asp His Glu Gly Glu His Phe Ser Val
        195                 200                 205

Pro Gly Pro His Gly Cys Glu Pro Ser Pro Gln Arg Thr Pro Val Ile
    210                 215                 220

Tyr Gln Ala Gly Ser Ser Asp Arg Gly Arg Glu Phe Ala Ala Ala Asn
225                 230                 235                 240

Ala Glu Ala Val Phe Ala Ser Gln Pro Thr Glu Glu Gly Val Arg Glu
                245                 250                 255

Tyr Val Thr Asp Val Lys Ser Arg Ala Ala Asp His Gly Arg Asp Pro
            260                 265                 270

Glu Ser Leu Arg Phe Phe Ile Gly Val Pro Val Val Gly Glu Thr
        275                 280                 285

Glu Ala Ala Ala Glu Ala Lys His Glu Ala Tyr Lys Ser His Val Asp
    290                 295                 300

Val Glu Ala Thr Leu Ala Leu Leu Ser Gly Phe Leu Asp Met Asp Leu
305                 310                 315                 320

Ser Glu Leu Asp Pro Asp Gln Lys Val Glu His Ile Glu Thr Asp Ala
                325                 330                 335

Ile Gln Gly Thr Met Asn Ala Phe Thr Lys Ala Gln Pro Asp Arg Glu
```

```
                    340                 345                 350
Trp Thr Val Arg Glu Val Ala Glu Phe Cys Gly Leu Gly Thr Thr Ser
            355                 360                 365

Pro Thr Ile Val Gly Thr Pro Glu Gln Val Val Asp Asp Leu Glu His
        370                 375                 380

Trp His Glu Ala Val Gly Val Asp Gly Phe Asn Val Lys Glu Val Val
385                 390                 395                 400

Arg Pro Asp Ser Leu Thr Asp Phe Val Asp Leu Val Val Pro Glu Leu
                405                 410                 415

Arg Glu Arg Gly Leu Val Pro Asp Pro Asp Ala Gly Asp Ser Pro
            420                 425                 430

Arg Gly Asp Gly Thr Leu Arg Glu Arg Leu Leu Gly Thr Gly Gln Ser
        435                 440                 445

Gln Leu Arg Asp Asp His Pro Ala Lys Gln
    450                 455

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctacgggag gcagcag                                                    17

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccccgtcaat tcmtttgagt tt                                              22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttccggttga tccygccgga                                                 20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
yccggcgttg amtccaatt                                                  19

<210> SEQ ID NO 8
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Met
<220> FEATURE:
<221> NAME/KEY: MOD_RES
<222> LOCATION: (4)..(4)
<223> OTHER INFORMATION: Any amino acid

<400> SEQUENCE: 8

His Glu Xaa Xaa His Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 9

Glu His Xaa Xaa Gly His His
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser or Ala

<400> SEQUENCE: 10

Leu Gln Arg His Xaa Asp His His Ala
1               5

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccttggaggt accaggaggt ttttattatg cggcgcgaaa gtctgttgg                49

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaccaaggtc tagatcatta tcaggacgca gccttcagcc atcg                    44
```

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccttggagtc gacctcgcgt tacgctcttt ctgt                                  34

<210> SEQ ID NO 14
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcccttgca aaccgatacc aacagacttt cgcgccgcat taaaatttcc tccttgaaat      60
gtgtt                                                                 65

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgcggcgcg aaagtctgtt ggtatc                                          26

<210> SEQ ID NO 16
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgagagctca agtaacggtt gagcgaaaaa taaaaagac ctggaataaa tccagatctt       60
taaatggaag caaattatca ggacgcagcc ttcagccatc                           100

<210> SEQ ID NO 17
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaagacaacc tgcaggcgga aaacacattt caaggaggaa attttaatgg aaataacttt      60
ttacccttta acggatgcac aa                                              82

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic

```
                                    primer

<400> SEQUENCE: 18
aacgtttacc tgcaggcttg tggttggtgt aaacttaatc c                        41

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccttggaaag cttctcgcgt tacgctcttt ctgt                                34

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaagacaacc tgcaggagtt acttggagga tactgtgagg agagacaatc ag            52

<210> SEQ ID NO 21
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgatccatat ttaaataaaa ttggggccct cctgaatatg gtgctcattg gtg           53
```

ALKALINE MICROBIAL ENHANCED OIL RECOVERY

CROSS REFERENCE TO RELATED APPLICATIONS

This application claims priority under Section 119(e) and the benefit of U.S. Provisional Application Ser. Nos. 61/446,674 filed Feb. 25, 2011, 61/496,461 filed Jun. 13, 2011, and 61/633,785 filed Feb. 17, 2012, the entire disclosures of which are incorporated herein by reference in their entirety.

FIELD OF THE INVENTION

The present invention is from the field of microbial enhanced oil recovery (MEOR). In particular, the invention concerns new, efficient, economical and environmentally safe microbial methods to enhance oil recovery, as well as microorganisms useful in such methods.

BACKGROUND OF THE INVENTION

The demand for crude oil has exceeded the existing production in the United States for more than 30 years, which has led to increasing demand for more imported oil and a dependency on foreign suppliers. Any new technology that could increase the efficiency of oil recovery would be of great benefit to countries such as the U.S. that have large amounts of unrecoverable oil in place (OIP) in older exiting oil fields.

Most of the remaining undeveloped oil in the Western Hemisphere is not light petroleum, but is heavy oil or tar sands. Large deposits of heavy oil are in Venezuela and California. Canada has large deposits of tar sands. Currently, production of heavy oil requires large amounts of energy.

Most petroleum is found in sandstone, siltstone or carbonate. Unlike natural gas, the recovery of petroleum oil is not efficient. The existing conventional oil production technologies are able to recover only about one-half of the oil originally in place in a reservoir of light oil. For heavy oil, the recovery is often less than 10%. Tar sands are so heavy that they will not flow at all and no oil can be recovered by conventional drilling and pumping. A technology that could recover a greater percentage of this residual oil could increase oil production from existing reservoirs and reduce the need of the U.S. for imported oil. The additional oil recovered from existing oil producing reservoirs could reduce the need to explore and develop wilderness areas that are potential new oil fields. This additional recovery of existing oil could bridge the gap needed for the development of alternative renewable energy sources.

The Original Oil In Place (OOIP) is the petroleum present in the oil reservoir when first discovered. The volume of the reservoir is determined by the size and porosity of the carbonate or sand stone. The porosity of the rock is a measure of the amount of small chambers or micro-traps within the rock that can hold water or oil. The oil is generally pushed up to the surface with the existing oil reservoir pressures at first, but the pressure in the oil well drops with time. Therefore, there is a need to create overpressure with other means such as water injection or a gas injection for secondary recovery of the OOIP. The choice of a specific secondary recovery technique depends on the type of the hydrocarbon accumulation and the nature of the reservoir. Water injection or "water sweep" or "waterflooding" is a common secondary recovery technique. In waterflooding, pressurized water is injected into the oil-bearing formation rock. Ideally, the injected water displaces the residual oil and moves it to a producing well. Generally in waterflooding, crude oil free of water is recovered first, and then subsequently a mixture of crude oil and water are recovered from the production wells. At some point, the percentage of water in the oil-water mixture (referred to as the water cut) from this technique becomes so high that it is uneconomical to continue pumping oil from the well. The problem, with using water as a "drive fluid", is that water and oil are immiscible. The lower viscosity water will flow over the oil and by-pass large amounts of oil. Therefore, even after secondary recovery, a significant portion of crude oil remains in the formation, in some cases up to 75% of the OOIP. The fraction of unrecoverable crude oil is typically highest for heavy oils, tar, and large complex hydrocarbons. In the U.S. this residual OIP in old oil wells could be as much as 300 billion barrels of light oil. World-wide, the estimate of unrecoverable oil is 2 trillion barrels. There are an additional 5 trillion barrels of heavy oil, most of which is unrecoverable. Much of this remaining oil is in micro-traps due to capillary forces or adsorbed onto mineral surfaces (irreducible oil saturation) as well as bypassed oil within the rock formation.

Enhanced Oil Recovery

Oil recovery by injection of fluids not normally found in the reservoir is referred to as Enhanced Oil Recovery (EOR). It is a subset of Improved Oil Recovery (IOR), which can include operational strategies such as infill drilling and horizontal drilling. Although it is sometimes referred to as tertiary recovery, it can be implemented along with secondary processes. Many types of EOR have been proposed and used over the years. Technical complexity and the high cost of chemicals have prevented the widespread use of EOR to where it only represents about 10% of total United States oil production.

There have been two major EOR approaches; thermal and non-thermal.

Thermal Processes

Thermal processes work by heating the reservoir rock and the oil to reduce viscosity of the heavy oil. In general, the lower the viscosity of the oil, the better its recovery will be. The most widely used thermal process is steam injection in which the temperature of the reservoir and the remaining oil is increased by heat energy of steam. Hot water may also be used, but it is not as efficient at transferring heat to the oil and rock in the reservoir. Unfortunately, in both processes, most of the heat energy is lost to the surroundings and does not go to heating the oil. In situ combustion of the oil is much more efficient than steam because it only heats the reservoir and not all the pipes and overburden rock. However, in situ combustion is difficult to control and is seldom used. Typically, it requires the energy equivalent of a half a barrel of oil to recover a barrel of oil with a steam injected thermal process. However, this depends on the oil saturation and the configuration of the reservoir. Because most of the energy carried by the steam is given up to the pipes, wall rock, and reservoir, it is best to use only on reservoirs with a high oil content so as to recover as much oil as possible with the steam used to heat the reservoir rock. Generally, thermal methods are used on heavy oil because it reduces the viscosity of the oil and increases the mobility of the oil and the mobility ratio (mobility of displacing fluid to mobility of displaced fluid or oil). Typically, recoveries are in the range of 50 to 60% for a thermal process, but the net energy gain is much less than that because of the large amount of energy needed to make steam. The ideal situation for thermal oil recovery is when there exists a nearby source of inexpensive or waste energy for steam generation.

Non-Thermal Processes

Non-thermal methods are best suited for light and moderately viscous oils. The major objectives for these processes are to lower the interfacial tension (IFT) between the oil and displacing fluid and to improve the mobility ratio. Many of the non-thermal processes experimented with or used over the years rely on surfactants for reducing the oil viscosity and decreasing the IFT between the oil and displacing fluid. Ideally, the mobility of the displacing fluid should not be higher than the oil. The mobility ratio (mobility of displacing fluid over mobility of displaced fluid) should be low. The mobility of the oil can be increased by viscosity reduction and by IFT reduction. As the IFT is decreased, the oil becomes more miscible with the fluid until it becomes one phase and the IFT is zero. This decreases the mobility ratio and increases the oil recovery. Alternatively, the viscosity of the displacing fluid can be increased by adding polymers to "thicken" the liquid. Non-thermal methods require less energy and are best suited for light oil of 100 cp or less. However, most non-thermal methods require considerable laboratory experimentation and process optimization. The high cost of surfactants and polymers is generally the limiting factor for chemical EOR.

There are two major classes of chemical or non-biological EOR. One is miscible flooding with a displacing fluid that is miscible with the reservoir oil and will reduce the IFT to zero. The displacing fluids can be solvents such as propane or pentane or compressible gases that are also soluble in the oil. The temperature of the reservoir must be low enough so that the gas can be compressed to a liquid at the pressure that the reservoir can withstand without fracturing. Some examples of compressible gases are: natural gas, flue gas, nitrogen and carbon dioxide. Carbon dioxide has been gaining in prominence in recent years, partly due to the possibility of green house gas sequestration. The amount of carbon dioxide required to recover oil is substantial (500-1500 $sm^3/sm^3$ oil). Although these processes can recover up to 20% of the OOIP, their use is limited to a fraction of all reservoirs due to reservoir pressure and temperature requirements and availability of gases. Currently, in over 80% of all carbon dioxide gas EOR projects, the gas is delivered to the well site by pipeline from deep carbon dioxide mines in a few locations in the US.

The other major class utilizes a chemical formulation as the displacing fluid. The chemical compounds interact with the oil or the water or both in such a way that there is a decrease in mobility ratio and IFT which leads to better oil mobility and recovery. Chemical methods have a major advantage over both thermal and compressed gases in that they generally have lower capital requirements and are not limited by location and availability of gases or sources of inexpensive heat energy. Economics is the major deterrent to the use of chemical EOR. Many of the chemicals used in these processes are manufactured from petroleum and their cost increases as the price of oil increases.

There are four major chemical flooding processes.

Polymer flooding functions by improving the mobility ratio and reducing the permeability contrast of the reservoir. In most cases a slug of polymer solution of about 20 to 40% of the reservoir pore volume is pumped into the injection wells. Losses of polymer to the porous reservoir rock and degradation of the polymer due to shear forces can limit the success of the method. The polymers can be synthetic chemical polymers such as polyacrylamide or biologically produced such as polysaccharides. Some bio-polymers are more effective at high salinity than the chemical polymers, but are also more expensive to produce.

Surfactant flooding is effective by lowering the IFT between oil and water. A surfactant molecule has a polar group on one end of the molecule and a hydrophobic regain on the other end of the molecule. The ideal surfactant is one that will reside in both the oil phase and water phase at the oil water interface. Petroleum sulfonates or other petroleum compounds with a charged or polar group are often used as surfactants. Excessive loss of surfactant to reservoir rock surface and the high cost of surfactant production have limited the use of this process. However, surfactants can be used in combination with other chemical EOR methods to increase the performance.

Alkaline flooding and alkaline-surfactant-polymer (ASP) flooding takes advantage of acid compounds naturally found in some petroleum. In alkaline flooding, an aqueous solution of alkaline chemicals, such as sodium hydroxide, sodium carbonate or sodium bicarbonate is injected into a reservoir. The alkaline chemicals react with the acid compounds, also referred to as naphthenic acid, of the crude petroleum oil to form in situ surfactants on the surface of the oil. This causes a reduction in EFT and sometimes a spontaneous emulsification of the oil. The alkaline flooding is followed by a slug of surfactant and polymers in solution which can significantly increase oil recovery. The alkali also reduces adsorption of surfactant onto the surface of the formation rock and thereby decreases cost.

This process is limited to oil that has sufficient organic acid to be transformed into suitable surfactants. The amount of acid in the petroleum reservoir oil can be determined by extraction with base and then titration by hyamine or by direct titration of acid in an organic solvent. This analysis generates an acid number which is defined as the milligrams of potassium hydroxide need to neutralize the acids present in one gram or oil. It is generally believed that the target oil must have an acid number of 0.4 or more to be amenable to alkaline flooding. However, this is only approximate because a simple acid number does not provide details on the type of acids present in the oil. The direct titration of all the acid in oil is called the total acid number (TAN) and is generally much higher than the extracted acid titrated with hyamine. The TAN number is misleading because large hydrocarbon acids are too lipophilic to be extracted from the oil by dilute sodium hydroxide solution. These large lipophilic acids will also not function as good surfactants or soaps at the oil-water interface. Small hydrocarbon acids are too hydrophilic to be detected by the hyamine titration and are also not useful as soaps because they move into the aqueous phase and do not help lower the IFT of the oil. Therefore the best measure of the naphthenic acid is an aqueous extraction and titration with hyamine.

For petroleum reservoirs that contain unrecovered oil with an extractable acid number of 0.4 or more ASP flooding can be the lowest cost chemical EOR process. Unfortunately, most petroleum reservoirs in the U.S. do not have a sufficiently high enough extractable acid to be amenable to ASP flooding. Some shallow oilfields have high TAN which is believed by some to be the result of many years of microbial degradation. However, this slow natural process has also removed most of the alkanes and other lighter oil compounds leaving the residual oil very viscous. In 1998 A. K. Stepp and T. French proposed a process of first biodegrading oil to increase the TAN in order that the oil would be more amenable to ASP or alkaline flooding. The limitation of this proposed two step process is that the lighter molecular weight alkanes and aromatic hydrocarbons will be converted faster to fatty acids than the higher molecular weight hydrocarbons. Another problem is that many of the fatty acids that are produced will also be utilized as a carbon source by the injected microbes and the indigenous microbes.

Another limitation of a two step process is the first step of biodegrading the oil to increase the acid content can be a long process taking many months or years. The actual time needed to complete the biological conversion of hydrocarbons to fatty acids is variable and unpredictable. The ability to determine the actual acid content in the residual oil trapped within the underground reservoir is limited. Drilling into the reservoir formation for oil analysis is very expensive and is not a reasonable meriting technique. Starting the alkaline flooding too soon before enough acid were generated would not produce enough oil recovery because the TAN was too low. Delaying the start of the alkaline process would cause more degradation of light hydrocarbons and a loss of the light oil fraction with an increase in viscosity which would also delay the start of oil production.

Therefore there is a need to combine microbial oil degradation with alkaline and ASP flooding in such a way that high oil recovery can be achieved without loss of oil to extensive bio-degradation or lengthy multistep processes. The need is for a new alkaline process that it can be used on a larger number of reservoirs and that would reduce the chemical cost of the surfactants and polymers.

Microbial Enhanced Oil Recovery (MEOR)

One special type of EOR technique uses microorganisms such as bacteria and Achaea to dislodge the micro-trapped or adsorbed oil from the rock. The goal of this technique, which is known as microbial enhanced oil recovery (MEOR), is to increase oil recovery of the original subsurface hydrocarbons using microbes rather than the more costly chemical recovery processes. These biological processes typically use microorganisms to achieve similar results as the chemical methods in that they reduce IFT and reduce the mobility ratio of the water drive fluid to oil. The major mechanisms by which microbes are believed to function by are: (1) alteration of the permeability of the subterranean formation by producing low molecular weight acids from the biodegradation of hydrocarbons that cause rock dissolution, (2) production of biosurfactants that can decrease IFT and form micelles of oil in water in a way similar to chemical surfactants, (3) mediation of changes in wet-ability of the oil droplet by growing on the droplet and changing the surface of the oil to a less hydrophobic surface (4) production of bio-polymers that improve the mobility ratio of water to petroleum by increasing the viscosity of water and plugging high flow channels, (5) production of lower molecular weight hydrocarbons by enzymatically converting the large hydrocarbons into smaller molecules, which will reduce of the oil's viscosity, (6) generation of gases (predominantly carbon dioxide and nitrogen) that increase formation pressure.

Of all the EOR processes, MEOR is presently considered the lowest cost approach, but it is generally the least often used. One of the limitations of MEOR processes that stimulate indigenous microbes is that there is little control of the six proposed mechanisms of biological oil recovery. It is also possible that other unknown mechanisms are responsible for the more successful field tests of MEOR. Without better understanding or control of this biological process it is unlikely to be used to recover oil from large oil fields. In order to be used as other chemical or thermal oil production processes, it would be best if each of the above mechanisms could be tested separately.

Numerous microorganisms have been proposed for achieving various mechanisms of the microbial mobilization process in subterranean formations. Field tests of these microbes involved injection of an exogenous microbial population into old and low producing oil wells. The inoculating culture was supplied with nutrients and mineral salts as additives to the water pumped into wells for oil recovery. The development of exogenous microorganisms has been limited by the conditions that prevail in the formation. Physical constraints, such as the small and variable formation pore sizes together with the high temperature, salinity and pressure of fluids in the formation and the low concentration of oxygen in the formation waters severely limit the types and number of microorganisms that can be injected and thrive in the formation. Later, it became apparent that indigenous microbes stimulated by the nutrients were playing the major role in oil recovery. Accordingly, it is difficult to determine which of the various biological mechanisms were at work.

Biological constraints, such as competition from indigenous microbes and the stress of changing environments (from surface to subsurface) also act to limit the viability of exogenous microorganisms. To overcome these problems, the use of indigenous microorganisms, commonly anaerobic, has been proposed in MEOR projects. It is known that bacteria and other microbes can grow indigenously within petroleum oil reservoirs and can be used to enhance oil production. It is also known that bacteria and other microbes will metabolize various components of petroleum as a carbon and energy source. In addition to the beneficial effects of making surfactants, solvents and other metabolites that can result in an increase in oil production; they can consume oil as a carbon source. Unfortunately, they generally prefer to consume the short-length alkanes.

In fact, the process of petroleum bio-degradation relies on the emulsification of oil so that the hydrocarbon can be transported into the bacterial cells for conversion to fatty acids as a carbon and energy source. This process can be used to remediate oil spills and other oil contaminated sites by supplying the indigenous microbes with nutrients or inoculating with cultures of microbes that can degrade oil. In the case of biological remediation of petroleum contaminated sites, microbes can produce metabolites such as surfactants that help emulsify oil so that they can then use the emulsified oil as a carbon source. Both of these functions help remove the hydrocarbon contamination from the site. However, in the case of MEOR only the production of metabolites such as surfactants, bio-polymers, hydrocarbon cleaving enzymes, organic acids and solvents are beneficial to increased oil production. Other than providing an energy source, the consumption of light petroleum is not beneficial to enhanced oil production from the reservoir.

The biodegradation of the shorter carbon alkane chains reduces the lighter fraction of the hydrocarbon mixture in the petroleum oil. The removal of the short chain alkanes from this mixture increases the overall viscosity of the hydrocarbon mixture. The higher viscosity mixture is more difficult to recover from the reservoir. The percent of recoverable oil is decreased. Also, oil that is recovered is more difficult to transport through pipes and to refine. Therefore the production of useful compounds, by microbes for improved oil recovery, comes with a high cost.

This process of stimulating all the indigenous microbes in an oil reservoir by adding nutrients is unpredictable. The growth of the microbes may produce the beneficial effect of dislodging oil entrapped within a petroleum reservoir. Alternatively, the light oil consumption may make the oil more viscous and lower the total recovery of oil.

It would be less detrimental if all petroleum components were degraded equally, but the case is that the shorter chain alkanes and lower molecular weight aromatics are more readily degraded by the microbes as carbon and energy sources. Therefore, unless genes that code for short chain alkane or light aromatics are absent in all microorganisms both injected and indigenous it is likely that light hydrocarbon degradation will be faster than heavy hydrocarbon degradation. This is supported by the fact that petroleum deposits near the surface, and most subject to biodegradation, are generally rich in high viscosity oil and contain high levels of asphaltic hydrocarbon and fairly low on light (short) chain alkanes. Canadian tar sands are believed to be the heavy residue representing about 10% of the original petroleum deposit from which 90% of the oil has been degraded.

In the past, others have taught ways of augmenting the growth of microbes that dislodge and mobilize oil from underground petroleum reservoirs. These methods generally recommend adding nutrients. Some have also taught adding various cultures of selected bacteria that added beneficial capabilities. Some have even reported isolating microbes that can only degrade higher molecular weight hydrocarbons (see, e.g. U.S. Pat. No. 5,013,654). However, adding these selected cultures is not enough to achieve the desired result. Although these prior methods disclosed that microbes do exist that can only feed on high molecular weight oil, they failed to provide methods of increasing the bio-digestion of heavy oils, while suppressing the lighter weight hydrocarbon consumption by other indigenous microbes. The microbes that are naturally residing within the petroleum reservoir are likely to have the ability to degrade lower weight oil. Adding nutrients will generally stimulate the growth of all the microbes present. Because the smaller hydrocarbons can be transported across the cell membrane, the light weight oil consuming microorganisms will grow faster than those consuming high weight oil and will dominate the population that results from stimulation.

There are no methods in the art that effectively prevent the faster biodegradation of the light weight low-viscosity oil in comparison to the slower biodegradation of the higher weight viscous oil in the mixed culture of a petroleum reservoir. There are reports of pure strains of microbes that degrade only heavy oil (Purwasena I. A., et al. *Proceeding of International Petroleum Technology Conference Doha*, Qatar Dec. 7-9, 2009). However, there is no method of preventing the growth of indigenous short chain degrading microbes generally resident in most reservoirs at less than 80° C.

Therefore, the same process that is beneficial to oil recovery is also detrimental to oil viscosity; and it is known that increasing the viscosity of the residual petroleum held within the reservoir will decrease oil recovery.

Accordingly, there is a great need for new enhanced oil recovery approaches that are energy efficient, and can be reliably and successfully used in large field situations to enable the recovery of currently unrecoverable oil in existing oil fields. This new method should be able to selectively degrade certain target compounds found in the oil remaining in the subject reservoir so that the oil will be modified for better recovery by waterflood or by a chemical waterflood. Furthermore, the genes and the enzymes they code for can be modified and their expression regulated to best transform the oil for better recovery and production. The host microorganisms should be selected so that they survive the extreme conditions in the reservoir at the time of waterflooding or during a chemical EOR waterflooding.

SUMMARY OF THE INVENTION

It is an object of this invention to provide microbes with genes for metabolic pathways that are useful for the enhanced recovery of petroleum oil from underground reservoirs, oil sands and other sources of heavy oil while suppressing the consumption of the lighter fraction of the petroleum. In addition, it is an object of this invention to give the host or recipient organism of these genes a competitive advantage for the specially modified environment of the hydrocarbon resource reservoir before and or during an alkaline waterflood oil recovery process.

In one aspect, the invention concerns a method of enhancing oil recovery comprising
  (a) inoculating an oil reservoir with a consortium comprising microbes that are obligatory alkaliphilic, halo-alkaliphilic or alkaline tolerant and are deficient in their ability to utilize short chain hydrocarbons of about 12 carbons or less but have the ability to convert hydrocarbons into fatty acids,
  (b) allowing the consortium to proliferate and degrade hydrocarbons of greater than 12 carbons, and
  (c) obtaining enhanced oil recovery from the oil reservoir.

In one embodiment, alkaline conditions are provided or are naturally present in the reservoir.

In a further embodiment, at least step (b) is performed under alkaline conditions.

In another embodiment, the consortium comprises microbes that are naturally alkaliphilic, halo-alkaliphilic or alkaline tolerant.

In another embodiment, the consortium comprises microbes that are engineered to be alkaliphilic, halo-alkaliphilic or alkaline tolerant.

In yet another embodiment, the consortium comprises microbes that are naturally deficient in their ability to degrade short chain hydrocarbons of about 12 carbons or less.

In a further embodiment, the consortium comprises microbes that are engineered to be unable to degrade short chain hydrocarbons of about 12 carbons or less.

In a still further embodiment, the consortium comprises microbes in which one or more metabolic pathways for degrading short chain hydrocarbons of about 12 carbons or less are down regulated or deleted or modified.

In a different embodiment, the consortium comprises microbes that naturally have the ability to degrade hydrocarbon chains of greater than about 12 carbons.

In another embodiment, the consortium comprises microbes that are engineered to be able to degrade hydrocarbon chains of greater than about 12 carbons.

In yet another embodiment, the consortium comprises microbes in which one or more metabolic pathways for degrading hydrocarbon chains of greater than about 12 carbons are introduced.

In a further embodiment, the consortium comprises microbes that are capable of utilizing high molecular weight hydrocarbons present in the oil reservoir as a carbon source.

In a still further embodiment, the consortium comprises microbes that are capable of growing in a high salt environment (halophiles).

In an emodiment, high salt environment is provided or is naturally present in the reservoir.

In a still further embodiment, the consortium comprises microbes are capable of utilizing simple carbons, where the simple carbons may, for example, be selected from the group consisting of glucose, sucrose, mannose, starch, glycerin, organic acids, and other simple sugars.

In a different embodiment, in step (a) a nutrient mixture comprising a soluble carbon source is injected into said oil reservoir along with the consortium, where the nutrient mixture may optionally further comprise at least one non-hydrocarbon nutrient, such as, for example, yeast extract, peptone, succinate, lactate, formate, acetate, propionate, glutamate, glycine, lysine, citrate, glucose, and/or vitamin solutions.

In a particular embodiment, the microbes are of the domain Archaea and/or are bacteria.

In other embodiments, the consortium is able to grow at pH of 9.0 or higher, or at pH of 10.0 or higher.

In various embodiments, the consortium may comprise microbes of the domain Archaea and/or bacteria that are obligatory alkaliphiles, halo-alkaliphiles or alkaline tolerant, and have the ability to utilize ring aromatic hydrocarbons and/or modified hydrocarbons containing sulfur and/or modified hydrocarbons containing nitrogen.

In another embodiment, the consortium comprises microbes of the domain Archaea and/or bacteria that are obligatory alkaliphiles, halo-alkaliphiles or alkaline tolerant, and have the ability to produce surfactants.

In still another embodiment, the consortium comprises microbes of the domain Archaea and/or bacteria that are obligatory alkaliphiles, halo-alkaliphiles or alkaline tolerant, and that have been engineered to produce surfactant. In one other embodiment, the production of surfactant is independent of the expression of genes that code for the degradation of hydrocarbons.

In yet another embodiment, the consortium comprises microbes of the domain Archaea and/or bacteria that are obligatory alkaliphiles, halo-alkaliphiles or alkaline tolerant, and have the ability to produce extracellular polymers.

In a further embodiment, the method of the present invention further comprises the step of water-flooding said reservoir with an alkaline fluid or a fluid containing a compound toxic to indigenous microbes to reduce the concentration of microbes that have the ability to utilize short chain hydrocarbons of about 12 carbons or less.

In a still further embodiment, the method of the present invention further comprises the step of adding to the reservoir at least one chemical inhibitor to control a metabolic pathway of at least one indigenous microbe present in the reservoir and/or obligatory alkaliphilic, halo-alkaliphilic or alkaline tolerant microbe inoculated into the reservoir.

In an embodiment, the chemical inhibitor inhibits the degradation of short-chain alkanes by said indigenous and/or inoculated microbe.

In another aspect, the invention concerns an isolated microorganism, preferably of the domain Archaea or bacteria, that (i) is an obligatory alkaliphile, halo-alkaliphile or alkaline tolerant, and (ii) is deficient in its ability to degrade short chain hydrocarbons of about 12 carbons or less.

In one embodiment, the microorganism is obligatory alkaliphilic, halo-alkaliphilic or alkaline tolerant and is deficient in their ability to utilize short chain hydrocarbons of about 12 carbons or less but has the ability to convert hydrocarbons into fatty acids.

The microorganism may naturally have the described properties and/or may be engineered to possess one or more of the described properties.

In various embodiments, the microorganism is able to grow in alkalinity of pH 9.0 or higher, or in alkalinity of pH10.0 or higher.

In another embodiment, the microorganism has the ability to utilize hydrocarbon chains of greater than 12 carbons.

In a further embodiment, the microorganism has the ability to utilize modified hydrocarbons containing sulfur.

In a still further embodiment, the microorganism has the ability to utilize modified hydrocarbons containing nitrogen.

The invention also concerns a consortium comprising microbes that possess one or more of the properties described above.

The invention further concerns a consortium comprising one or more types of microorganisms as hereinabove described.

In a further aspect, the invention concerns an oil reservoir, comprising a consortium herein.

The consortium used in the methods herein may contain one or more different types of microorganisms. Thus, for example, it may contain microorganisms that are both obligatory alkaliphilic, halo-alkaliphilic or alkaline tolerant and halophiles, in addition to being deficient in their ability to utilize short chain hydrocarbons. It is also possible, however, that the consortium contains two different types of microorganisms, one being obligatory alkaliphilic, halo-alkaliphilic or alkaline tolerant and deficient in their ability to utilize short chain hydrocarbons, and the other one being a halophile which is also deficient in its ability to utilize short chain hydrocarbons.

It is noted that two or more of the various embodiments listed above or otherwise disclosed herein can be used in any combination, and any and all of such combinations are within the scope of the present invention.

It is further noted that various embodiments described in connection with one aspect of the invention are also contemplated with respect to other aspects of the invention. Thus, embodiments described with reference to the methods of the present invention also apply to other aspects, such as the consortium of microorganisms or the isolated microorganisms present in such consortium, as applicable.

BRIEF DESCRIPTION OF THE DRAWINGS

The patent or application file contains at least one drawing executed in color. Copies of the patent application publication with color drawing(s) will be provided by the Office upon request and payment of the necessary fee.

FIG. 4 shows the alignment of the amino acid sequences of the LadA long chain alkane monooxygenase (SEQ ID NO: 1) with the hypotheical protein Gen ID 9420269 HacjB3_12265 from *Halalkalicoccus jeotgali* B3 alkalitolerant halophiles (SEQ ID NO: 2) and with another hypothetical protein from the halophile, *Halorubrum lacusprofundi* (ATCC 49239) Gene ID 7401614 Hlac 0096 (SEQ ID NO: 3).

DETAILED DESCRIPTION OF THE INVENTION

I. Definitions

Figure 1:
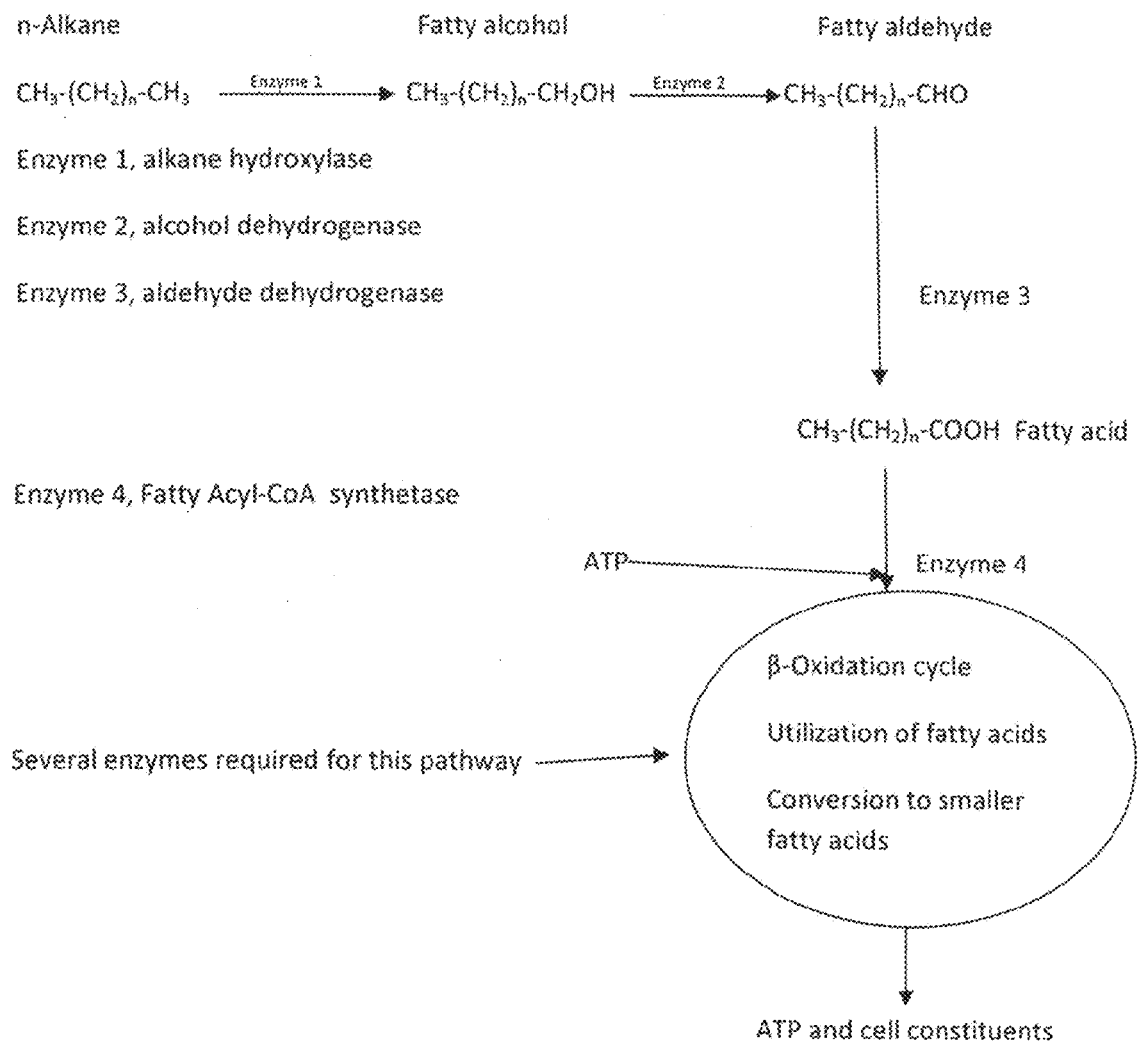
FIG. 1 illustrates a pathway for the degradation of alkanes by microorganisms.
Figure 2:
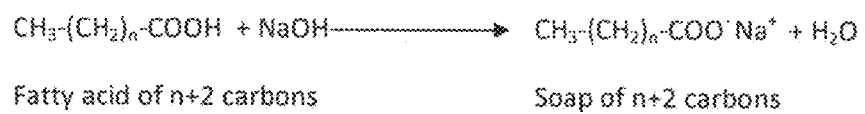
FIG. 2 illustrates the conversion of fatty acids to soap at alkaline pH.
Figure 3:
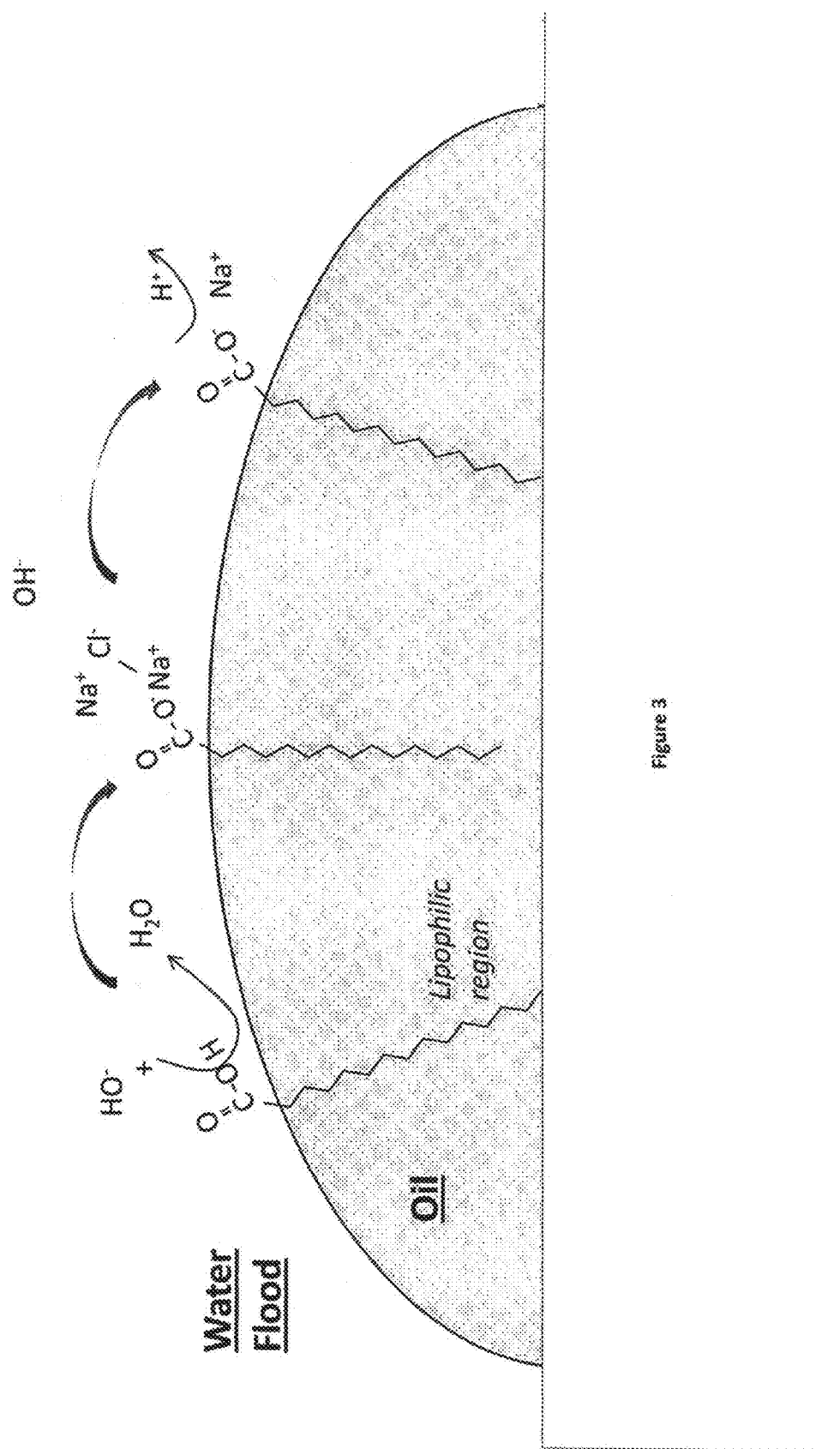
FIG. 3 illustrates the emulsification of oil by fatty acid soaps at alkaline pH.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. Edition (1989) Cold Spring Harbor Laboratory Press, Cold Spring Harbor, N.Y. Also, for example, Current Protocols in Molecular Biology, Supplement 93, January 2011, John Wiley & Sons, Inc. As appropriate, procedures involving the use of commercially available kits and reagents are generally carried out in accordance with manufacturer defined protocols and/or parameters unless otherwise noted.

It must be noted that as used herein and in the appended claims, the singular forms "a", "and", and "the" include plural referents unless the context clearly dictates otherwise.

Throughout this specification and claims, the word "comprise," or variations such as "comprises" or "comprising," will be understood to imply the inclusion of a stated integer or group of integers but not the exclusion of any other integer or group of integers.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

The term "oil reservoir" is used herein in the broadest sense and includes all forms of hydrocarbon deposits, including, without limitation, producing wells, non-producing wells, experimental wells, exploratory wells, and the like, which may be accessible by any means, such as, for example, one or more wellbores.

The term "crude oil" refers to a naturally occurring, flammable liquid found in rock formations and comprises a complex mixture of hydrocarbons of various molecular weights, plus other organic compounds. Without limitation, the crude oil may contain, for example, a mixture of paraffins, aromatics, asphaltenes, aliphatic, aromatic, cyclic, polycyclic and/or polyaromatic hydrocarbons. The crude oil may be generic or may be from a reservoir targeted for enhanced oil recovery in accordance with the present invention.

The terms "well" and "reservoir" may be used herein interchangeably and refer to a subterranean or seabed formation from which oil may be recovered. The terms well and reservoir include the physical/chemical composition of the soil-rock-sediment structure of the reservoir below the surface.

The term "environmental sample" means any substance exposed to hydrocarbons, including a mixture of water and oil comprising microorganisms. As used herein, environmental samples include water and oil samples that comprise indigenous microorganisms and/or populations of microorganisms of varying genus and species. The environmental samples may comprise a microbial consortium unique to a geographic region or target reservoir, or, alternatively the microbial consortium may be adaptable to other environment sites, geographies and reservoirs.

The term "microbe" is used herein in the broadest sense and includes all microorganisms, including bacteria, fungi, archae, and protists, and microscopic animals, such as plankton, planarian and amoeba. Preferred microbes for the purpose of the present invention are bacteria and archae.

The term "microbial consortium" is used herein to refer to multiple interacting microbial populations. Members of a consortium communicate with one another. Whether by trading metabolites or by exchanging dedicated molecular signals, each population or individual detects and responds to the presence of others in the consortium. This communication enables a division of labor within the consortium. The overall output of the consortium rests on a combination of tasks performed by constituent individuals or sub-populations.

Archaea comprise one of the three distinct domains of life, with bacteria and eukaryotes. For a review, see, e.g. Makarove and Koonin, *Genome Biology* 4:115 (2003).

The term "alkali tolerant" is used herein to refer to an organism capable of growing at pH of 9 or more, but with optimum growth rates at neutral pH.

The term "obligatory alkaliphile" (also spelled alkalophile) is used herein to refer to an organism whose growth is optimal in at least two pH units above neutrality or a pH of 9 or more.

The term "obligatory haloalkaliphile" is used herein to refer to an organism whose growth is optimal at a salt concentration of 100,000 ppm or more and at a pH of 9.0 or more.

For a review of alkaliphilic and alkalitolerant microorganisms see, e.g. Koki Horikoshi, Microbiology and Molecular Biology Reviews, December 1999, p. 735-750. And "Alkaliphiles" 1999 ISBN 90-5702-458-6 published by Kodanha Ltd Tokyo Japan, author Koki Horikoshi.

The term "halophile" is used herein to refer to an extremophile that thrives in environments with very high concentrations, typically at least about 5% (50,000 ppm), or at least about 10%, or at least about 15% of salt.

The term "obligatory halophile" is used herein to refer to an extremophile whose growth is obligately dependent on high salt concentrations, typically at least about 5% (50,000 ppm), or at least about 10%, or at least about 15% of salt.

The terms "repression" and "inhibition" with reference to gene expression are used herein interchangeably and refer to any process which results in a decrease in production of a gene product, regardless of the underlying mechanism. A gene product can be either RNA or protein. Gene repression includes processes which decrease transcription of a gene and/or translation of mRNA. Thus, specifically included in this definition are processes that inhibit the formation of a transcription initiation complex along with those that decrease transcription rates and those that antagonize transcriptional activation is gene repression. These repressions can be either reversible or irreversible, both of which are specifically included in this definition. The repression can be partial with only lower levels of the gene expressed or complete with no genes expressed and no protein gene product synthesized.

The term "lateral gene transfer" is used herein in the broadest sense and refers to the transmission of genetic information from one genome to another.

The term "surfactant" as used herein means microbially produced surface-active agents, including, but not limited to, glycolipids (e.g. sophorose lipid or rhamnose lipid), lipoproteins, polysaccharide-fatty acid complexes, mono- and diglycerides, lipoheteropolysaccharides, peptidolipids, neutral lipids, corynomycolic acids, trehalose dimycolates and polysaccharide-protein complexes.

The term "soap" is used herein in the broadest sense to describe any hydrocarbon with one or more carboxyl groups, or also referred to as a fatty acid, that has been converted to the acid salt by alkaline removal of the hydrogen ion and replacement with a mono or divalent metal ion.

The term "hydrocarbon" is used herein in the broadest sense to describe any organic compound that contains only carbon and hydrogen (in some cases may contain sulfur or nitrogen atoms). The term specifically includes, without limitation, saturated hydrocarbons (alkanes), unsaturated hydrocarbons (including alkenes and alkynes), cycloalkanes, and aromatic hydrocarbons (arenes).

The term "short chain hydrocarbon" is used herein to mean both strait chain alkanes or branched chain alkanes containing 12 carbons or less.

A "short chained alkane", as defined herein, contains 1 to 4 carbon atoms.

A "high molecular weight hydrocarbon", as defined herein, is a hydrocarbon having at least about 40 carbons, for example, a hydrocarbon having between about 40 and about 60, or between about 40 and about 80, or between about 40 and about 100, or between about 40 and about 120 carbons.

The term "waterflooding" is used herein to refer to a crude oil recovery process wherein a fluid containing water is pumped into an injection well in contact with an underground formation containing crude oil to drive the residual crude oil towards another well also in contact with an underground formation for the purpose of producing oil.

The term "nutrient supplementation" refers to the addition of nutrients that benefit the growth of microorganisms that are capable of using crude oil as their main carbon source but grow optimally with other non-hydrocarbon nutrients, i.e., yeast extract, peptone, succinate, lactate, formate, acetate, propionate, glutamate, glycine, lysine, citrate, glucose, and/or vitamin solutions.

II. Detailed Description

The present invention concerns enhanced methods for microbial oil recovery, characterized by the use of microbes that are obligatory alkaliphilic, halo-alkaliphilic or alkaline tolerant and additionally are deficient in their ability to utilize short chain hydrocarbons while having the ability to convert hydrocarbons into fatty acids. The latter property is useful for emulsifying the oil at alkaline pH.

In certain embodiments of the present invention, means are provided to utilize an alkaline microbial waterflooding process to mobilize oil remaining in a petroleum reservoir. In this microbial process the acid content of the crude oil is increased by microbial degradation of the hydrocarbons at alkaline pH. Microorganisms preferred for this process are selected or engineered to convert oil hydrocarbon components to alcohols, aldehydes, ketones and/or fatty acids that are the most useful at alkaline pH to aid in the emulsification and dispersion of oil into the waterflood drive fluid. At alkaline pH the preferred size range of fatty acids are converted to soaps which can reside at the oil to water interface. Smaller hydrocarbons are converted to only alcohols or aldehydes which do not have a negatively charged carboxyl group such as fatty acids. These low molecular weight alcohols of about two to eight carbons are more useful as co-surfactants than the corresponding low molecular weight fatty acids. The methods provided by the present invention are designed to select the preferred size range of hydrocarbons modified by the microbial consortium and direct the pathways to produce the products that are most beneficial for oil emulsification and reduction of interfacial tension.

According to the present invention, certain metabolic pathways such as pathway(s) required for complete degradation of short chain alkanes are selected out of microorganisms present in a consortium. As a result, the consortium will contain microbes that are not only obligatory alkaliphilic, halo-alkaliphilic or alkaline tolerant, but are also deficient in their ability to utilize short chain hydrocarbons (e.g. less than about 20 carbons, or about 12 carbons or less).

In particular, bacteria and other microbes (e.g. Archaea) are carefully selected or modified to be deficient in their ability to consume the lower weight hydrocarbons all the way through the $\beta$-oxidation pathway. Fatty acids that enter the $\beta$-oxidation pathway by conversion to Acyl-CoA can be converted to energy for cell growth. A method of engineering a pathway into *E. coli* for production of fatty acids and fatty alcohols and other bio-fuels is described by Eric J. Steen et al. in "Microbial production of fatty-acid-derived fuels and chemicals from plant biomass" *Nature* 463, 559-562 (28 Jan. 2010) doi:10.1038/nature08721: and is incorporated by reference. The referenced report is an example of knocking out a gene for $\beta$-oxidation of fatty acids for the purpose of producing an accumulation of fatty acids and alcohols for biofuel production. Fatty acids in a range of C8-C18 are reported in concentrations as high as 0.3 g/l.

The preferred products of bioconversion are short chain alcohols which are useful in reducing the viscosity of oil and functioning as a co-surfactant in emulsifying oil. A consortium of microbes is selected, modified or controlled so that the microbial culture relies on either a soluble carbon source provided by the nutrient mixture injected with the microbes and water flood or the bio-consumption of high molecular weight hydrocarbons present in the petroleum. The metabolic pathways that degrade only the higher molecular weight hydrocarbons are not deliberately down regulated or deleted. These pathways are beneficial because the consumption of higher molecular weight carbohydrates provides an additional carbon source, and the removal of high molecular weight oil reduces the viscosity of the oil. Reduction of viscosity improves both the value and the recovery of the petroleum.

In addition, the conversion of hydrocarbons in the range of C-13 to C-40 to fatty acids is useful for the emulsification of oil at alkaline pH. This range of fatty acids is small enough to be extracted from the oil droplet and react with the alkaline material to form soap by loss of a proton. The preferred size range of the fatty acids can be refined for the temperature, salinity and other environmental factors anticipated in the reservoir. This refinement can be made by laboratory experimentation by addition of various fatty acids such as hexadecanoic acid to reservoir petroleum oil samples (as described in Example 3) and measuring interfacial tension with the drive fluid. In addition to determining the preferred size range by a determination of IFT reduction of oil and drive fluid, oil with various levels (acid number defined as mg of KOH per gram of oil needed to neutralize the acid) and types (number and configuration of carbons atoms) of fatty acids can be analyzed for recovery in sand pack columns or core flood laboratory experiments. The advantage of these experiments is that they can be used to quickly determine the size range for each type of fatty acid or fatty alcohol that will be most beneficial for emulsifying the type of oil found is various reservoirs. Also the pH and salt concentration can be evaluated for the drive fluid to be used in field oil recovery process.

These size ranges for each type of hydrocarbon, that will yield the most effective increase in oil recovery at the conditions anticipated in the actual oil field application, can then be used to select metabolic pathways for placement and expression of genes for the needed enzymes in the host engineered microorganism. The engineered host microorganisms can then be tested in the laboratory to determine if they can grow on the type of oil found in the target reservoir and increase the fatty acid content of the oil as it degrades it. The conversion of oil substrate molecules into fatty acids and fatty alcohols can be determined by gas chromatography of the oil, liquid chromatography of the aqueous phase or by basic aqueous extraction of the fatty acids from the oil followed by making a derivative for gas chromatography. Direct mass spectrometry or in combination with gas or liquid chromatography is also a possible way to analyze and quantitate the fatty acids and alcohols formed by microbial degradation of the petroleum. By these methods, each strain of engineered microbe can be evaluated for its ability to transform the oil into an acid number that is higher than the native oil.

Not only will the total acid number be increased, but the size range of acids can be made of the size that is best for decreasing IFT between the oil and drive fluid. Small acid products that are too hydrophilic to reside at the oil surface would move into the hydrophilic drive fluid, and would not be useful for oil recovery. In addition they might be detrimental by reducing the pH of the drive fluid. At the other extreme, very large hydrocarbons may be so hydrophobic that they would reside entirely in the oil phase and not effectively contribute to the extractable acid number or help in lowering the IFT of the oil. Therefore, the oil that is degraded and transformed into acids will be very useful for improving oil emulsification at alkaline conditions. Therefore, the total oil remaining will become a better target for alkaline flooding or alkaline surfactant polymer flooding.

The oil recovery process wherein the drive fluid is maintained at an alkaline pH is referred to as alkaline flooding. The oil recovery process wherein the drive fluid also contains a chemical polymer and a chemical surfactant in combination with and alkaline drive fluid is referred to as alkaline surfactant polymer waterflooding or ASP waterflooding. The aqueous drive solution is an alkaline chemical, such as sodium hydroxide, carbonate or bicarbonate. The alkaline chemical reacts with the acid compounds in the crude oil and produces the surfactant in situ. IFT reduction is the main mechanism of oil emulsification. The process is complex due to various reactions with the reservoir rock and fluids. Adverse interactions with the reservoir rock can be minimized by use of moderate pH alkaline chemicals, such as sodium carbonate and bicarbonate. When this process is combined with the additional chemical formulations of an added chemical surfactant and chemical polymer (ASP) the major recovery mechanisms are both IFT reduction and improvement in mobility ratio. Both methods require that the reservoir oil have an acid number of 0.5 or more to be economically effective. A more detailed description of alkaline flooding for EOR was reported by J. Xie, B. Chung, L. Leung at the Society of Petroleum Engineers International Thermal Operations and Heavy Oil Symposium held in Calgary, Alberta, Canada, 20-23 Oct. 2008 and is available from the SPE in publication SPE/PS/CHOA 117221 PS2008-323.

In addition to transforming the native oil into one of higher acid content, especially of the type of acids (soluble to some degree in both the oil and the water phase and having both a lipophilic and a hydrophilic region) that are best suited for soap formation during an alkaline flooding or ASP flooding, another embodiment is the simultaneous increase of the acid content of native oil while an alkaline process is ongoing. During the alkaline process, the alkaliphile microbes grow on the oil surface and produce the range of fatty acids that aid the emulsification of oil. Because this happens on the other surface of the oil liquid, small droplets of oil can form and be emulsified into the alkaline water. This process then exposes a new oil surface to the growing microbes. In this way the alkaliphiles can bore into the oil faster as the oil droplets are removed by the alkaline water. The faster the microbes are at converting hydrocarbons into fatty acids the faster they are at emulsifying the entire oil layer. Therefore a microbe that can grow rapidly at alkaline pH will recover more oil and at a faster rate than a microbe that must convert hydrocarbons to fatty acid at neutral pH to be followed by an alkaline waterflood.

In addition to the facilitation of emulsifying soaps from the fatty acids at alkaline pH, the high pH also acts to kill off or suppress the growth of indigenous microbes. Microorganisms that have adapted to extreme environments such as high pH and high concentrations of salt often have evolved with significant changes to their protein amino acid sequences. Alkaliphiles and haloalkaliphiles enzymes are significantly higher in negatively charged amino acids and low in the positively charged amino acid lysine, which helps prevent the acquisition of genes for light chain oil utilization enzymes.

If the inoculating microbes lacked certain unwanted genes, but the inoculating microbes were similar to the indigenous microorganisms, they could pick up unwanted genes from the indigenous microorganisms. Even if the engineered culture was robust and quick growing, it could acquire genes that coded for the metabolism of light weight oil. This could occur by the process of Lateral Gene Transfer (LGT), which is known to occur in many natural environments. Picking up such genes would give the microbes a competitive or evolutionary advantage, and they would soon dominate the population.

By the use of alkaline fluids and microbes that prefer alkaline conditions, this invention provides a means for preventing LGT so that the engineered or selected culture of microbes with the desired properties does not acquire unwanted or detrimental pathways for improved oil production. Lateral gene transfer is common among bacteria and Archaea as a mechanism of genetic information sharing between different species. It is believed to play a significant role in evolution and is also known to occur in higher organisms. The prevention of LGT is an important part of the successful implementation of engineered microorganisms.

By preventing the metabolism of light oil, the corresponding viscosity increase, caused by the removal of the light oil fractions, is also prevented. As stated above, the higher the viscosity of oil, the lower the recovery will be. The beneficial effects of the microbes such as reduction of IFT, increase sweep efficiency and improved mobility ratio could be negated by increase in viscosity. However, if the microbes can only consume heavy oil or other carbon sources, the major detrimental effect can be avoided. This makes the MEOR process of the present invention more predictable and more effective.

The use of an obligate alkaliphile or halo-alkaliphile or alkaline tolerant microorganism requires that certain genes taken from a non-alkaliphile or neutral pH microbe be removed or modified to change the amino acid sequence of any proteins they code for. These changes are needed to render the proteins functional at a higher pH. These required changes can be determined by analysis of homologous proteins found in both neutral pH and alkaline pH microorganisms. In addition, three dimensional structural analyses can be used to determine surface positively charged resides such as lysine which may be changed to negatively charged amino acid residues such as aspartic acid. This type of amino acid residue changes will result in an increase negative charge, which is generally beneficial to high salt and high pH functionality. A large number of potentially beneficial changes can be made and then tested by expression in a model alkaliphile or halo-alkaliphile such as *Natronobacterium magadii* and *N. gregoryi*.

The study of hydrocarbon bio-degradation provides an understanding of the mechanism of short chain alkane metabolism. The shorter chain alkanes are made soluble in water generally with the aid of surfactants produced by the bacteria or Archaea. Then, the soluble alkane adsorbs onto the cell's hydrophobic membrane and is transported across the membrane of the microbe. Enzymes at the membrane convert the alkane to an alcohol. Subsequent chemical reactions catalyzed by other enzymes convert the alcohol to an aldehyde and then to an organic acid, also referred to as a fatty acid. The fatty acid can then be further metabolized by the cell for energy and carbon building blocks for its growth. This biology of the short chain alkane metabolism is the most studied and the best understood. Metabolism of larger or higher molecular weight hydrocarbon is more complex and less well understood. The larger or higher weight hydrocarbons are much less soluble and more difficult to transfer across the cell membrane. However, the biodegradation of high molecular weight oil is known to occur, however, it happens at a slower rate. A more detailed description of biological degradation of hydrocarbons is reviewed by J. D. Van Hamme, A. Singh, and O. Ward in *Microbiology and Molecular Biology Reviews*, December 2003, p. 503-549, Vol. 67 No 4, DOI: 10.1128/MMBR.67.4.503-549.2003. This invention relies on retarding the light chain alkane metabolism by the engineered or selected microbes. The preferred modification is to stop the conversion of alkanes in the range of two to eight carbons at the corresponding two to eight carbon alcohol and to transfer it to the oil to water interface where it can function to reduce the viscosity of the oil and act as a co-surfactant.

In certain embodiments of the methods of the present invention, genes that code proteins in the alkane hydroxylase pathway, which are capable of degrading light weight and low viscosity hydrocarbons, are inhibited, e.g., deleted, mutated or down regulated in the selected or engineered microbe. In addition, LGT from the environment is prevented because the indigenous enzymes are less active at the higher pH. That is, the acquisition of similar genes that code for degradation of light weight oil from other neutral pH microbes are unlikely to be functional at the high pH of the alkaline microbes. However, the production of surfactants, co-surfactants or other metabolites, beneficial to oil mobilization, is not prevented. The expression of genes needed for the production of surfactants is maintained without the consumption of low viscosity oil.

Different sets of genes code for each of the different metabolic pathways that make it possible for microbes to feed on hydrocarbons as an energy source. The degradation and consumption of the higher molecular weight hydrocarbons is generally enabled by different genes then those that code for the light chain metabolic pathways. Genes that code for the enzymes required for hydrocarbon degradation and the genes for surfactant production may be regulated by the same promoters. However, with current molecular biology technology it is possible to move and separate each set of genes so that they can be independently controlled.

The enzymes that degrade hydrocarbons have different substrate specificities. The first step in the degradation of alkanes is the oxidation of either the terminal carbon or an internal carbon to form a primary or secondary alcohol. The monooxygenases are one type of enzyme that catalyze the first step in the metabolism of hydrocarbons and have binding sites that show a preference or specificity for different lengths of straight chain alkanes. In addition, there are monooxygenases that will oxidize aromatic hydrocarbons of different sizes. Many of the genes have been isolated and their sequences characterized. Many others have not yet been isolated, but are expected to have similar sequences and different specificities. With probes for genes based on highly conserved regions of protein sequences of key enzymes and protein sequences that determine substrate specificity, new genetic information can be obtained from microbes inhabiting petroleum sites.

Currently, there is nucleotide and amino acid sequence information available for many monooxygenases that degrade different sizes and types of petroleum hydrocarbons that highly conserved regions have been identified. Highly conserved regions of protein sequences have been identified that are required for catalytic activity. Others are substrate specific and will vary with the size and type of hydrocarbon that they oxidize. For example, the 8 histidine amino acid residues that are required for catalytic activity in all alkane monooxygenases are in three histidine boxes (Hist1, HE[L/M]XHK (SEQ ID NO: 8); Hist2, EHXXGHH (SEQ ID NO: 9); and Hist3, LQRH[S/A]DHHA (SEQ ID NO: 10)) reported by J. B. van Beilen et al in *Applied and Environmental Microbiology*, December 2002, p. 5933-5942, Vol. 68, No. 12, DOI 10.1128/AEM.68.12.5933-5942.2002. This knowledge can be used to search for microbes within an environment that can degrade various hydrocarbons. Metagenomic sequencing of the environmental samples can be carried out, and new oxygenase genes identified by DNA sequence homology. Probes to the highly conserved sites can be used to isolate genes that code for monooxygenases that exist within the microbes inhabiting alkaline and petroleum containing sites. For example, alkaliphilic and halophilic hydrocarbon-utilizing microbes were isolated from oily alkaline intertidal areas of the Kuwaiti coasts by H. Al-Awadhi et al. in Applied Microbiol Biotechnology (2007) 77:183-186. Further analysis based on sequences of the substrate specific sites can identify genes that code for higher molecular weight hydrocarbon utilization at high pH.

Although slower than light chain utilization, degradation of heavy chain hydrocarbons can provide a supplemental carbon source without detriment to the viscosity or the value of the petroleum oil. Microbes have been isolated that can grow only on heavy petroleum components. These have been shown to have genes that code for enzymes that are specific for certain heavier hydrocarbons and to lack the genes for utilization of the lighter short chain alkanes. For example, L. Wang et al. reported isolating *Geobacillus thermodenitrificans* NG80-2 from a deep subterranean oil reservoir in northern China that degrades and metabolizes only long chain (C15-C36) n-alkanes, but not short-chain (C8-C14) n-alkanes. The complete genome sequence of *G. thermodenitrificans* NG80-2 has been deposited in the GenBank database and is incorporated with the corresponding publication in *Proc Natl Acad Sci USA*, Mar. 27, 2007 p. 5602-5607 by reference. Comparison of protein sequences can be done to identify specific substrate sequences and probes can be made to the genes for either short or long chain alkane monooxygenases. These probes can be used to screen DNA isolated from a specific site or oil reservoir. By this method and other methods of microbiology, the microbes that are responsible degradation of heavy and light oil in a reservoir can be identified. For example, by searching GenBank with the protein sequence of LadA, a long alkane monooxygenase, from the thermopile and non-halophile, *Geobacillus thermodenitrificans* NG80-2, a protein sequence with 49% identity to LadA with most of the amino acids resides at the putative reactive site and flavin binding site identical to the amino acid residues found in *Halalkalicoccus jeotgali* (DSMZ 4425), which is a alkaliphile and a halophile. Another hypothetical protein sequence from the genome of *Halorubrum lacusprofundi* (ATCC 49239), which is reported to be a halophile but not an alkaliphile, is also 49% identical in protein sequence and nearly identical at the putative active pocket to the monooxygenase found in *G. thermodenitrificans* NG80-2. By comparing sequences of homologous proteins from alkaline pH environments to neutral environments, predictions can be made for changes to surface amino acid residues that will adapt the proteins for higher pH optimums. This type of sequence information can be used to engineer amino acid changes to make neutral pH and low salt enzymes functional at either high pH or high salt and high pH. Each of the modified sequences can be expressed as new enzymes that can be analyzed for its pH optimum and salt solubility.

In addition to high molecular weight hydrocarbons, petroleum oil contains compounds that are not desirable to have in oil that will be refined into various petroleum products. One major group of undesirable compounds is modified hydrocarbons high in sulfur. Sulfur can be the third most abundant element in crude oil and is especially high in heavy oil. Lowering the sulfur content would increase the value of the crude oil. Bacteria that are capable of selectively attacking the C—S bonds have been isolated and their metabolic pathways elucidated. Most strains studied have been aerobically grown and include; *Rhodococcus erythropolis, Nocardia* spp., *Agrobacterium* sp. Strain MC501, *Mycobacterium* spp., *Gordona* sp. Strain CYKS1, *Klebsiella* spp., *Xanthomonas* spp., and the thermophile *Paenibacillus*. These bacteria have been shown to be effective at desulfurization of various sulfur containing hydrocarbons found in crude oil. However, the process is a two phase oil and water system that requires surfactants and energy-intensive mixing. To achieve a sulfur removal rate of over 50% high water to oil ratios were needed in well mixed and aerated reactors. Important aspects of the process include reactor design, product recovery and oil-water separation.

Another group of undesirable hydrocarbons are nitrogenous compounds. Crude oil can contain about 0.5% to 2.1% nitrogen with 70% or more as pyrroles, indoles and carbazole nonbasic compounds. These compounds are poisons to cracking catalysts, toxic and result in air pollution. Removal of the nitrogenous compounds would increase the value of oil recovered by the MEOR process. Several species of bacteria have been isolated that contain metabolic pathways for the oxidative transformation of nitrogenous compounds found in crude oil. A review of these bacterial processes was published by Kaiser, J. P. et al. in *Microbiol. Rev.* 60:483-498. The genes responsible for carbazole degradation by *Pseudomonas* sp. strain CA10 were identified and cloned into *E. coli* by Sato et al and were reported to transform a wide range of aromatic compounds. The results are published in *J. Bacteria* 179: 4841-4849 in 1997.

The alkaline adaptation of enzymes needed for the desulfurization pathways or denitrogenation pathways can be done make the proteins functional s in the high pH environment of the host alkaliphile. Their incorporation into a culture designed for oil recovery can also reduce the sulfur or the nitrogen content of the recovered oil. However, because these are oxidative processes, it is important that genes responsible for light chain metabolism be eliminated so that the short chain alkanes are not rapidly degraded.

Many microbes that utilize hydrocarbons can also utilize simple and soluble carbon sources. Generally, when the concentration of a simple carbon source is high enough, the expression of all the genes needed for the utilization of hydrocarbons is down regulated. Some examples of soluble carbon sources comprise simple sugars, glycerin, starch, fatty acids and other organic molecules. This is one mode of preventing short chain alkane utilization as long as simple carbon sources are maintained at a high concentration. If the host or recipient microbe, engineered for the oil reservoir environment, does not contain adequate pathways for the utilization of inexpensive soluble carbon sources, genes required for those pathways could be transferred into the host microbe.

That is, by providing a soluble carbon and energy source at sufficient levels to maintain living cells and cell growth, the indigenous microbes may become nondependent on alkane hydrocarbon metabolism for growth and survival. This could lead to down-regulation and low expression of genes or even loss of the genes that code for enzymes that make useful metabolites such as surfactants that emulsify the insoluble hydrocarbons.

Therefore, a means for maintaining high expression of genes and levels of certain proteins must be provided. This can be done by a number of molecular biology techniques, including, but not limited to, placing the genes coding for each of the metabolic products such as surfactant production under the control of an inducible or constitutive promoter. This will allow for high expression by both transcription and translation of these genes. This provides means for preventing a down regulation that can occur with the wild type promoter when the cell detects a high level of easier to metabolize or preferred carbon source. In conventional MEOR processes that use only naturally occurring cultures of oil consuming microbes in combination with indigenous microbes present in the oil reservoir, the addition of too much of a simple carbon source, such as molasses, could lead to a reduction of surfactant production and unexpectedly lower oil emulsification.

The problem with relying on naturally occurring microbial processes is that they become less effective at both oil degrading and oil recovery when they are supplied with an easily metabolized carbon and energy source, such as molasses. However, not supplying any simple carbon source could slow growth and also lead to low oil production. In addition, the lack of a supplied carbon source will select for the strains of microbes that can utilize the hydrocarbons that exist within the oil reservoir. Furthermore, microbes that have genes that enable them to consume light weight oil will grow and multiply faster than any microbe, added or indigenous, that only contains genes for heavy oil consumption. Therefore, it is best to provide adequate carbon sources for the engineered or selected strains so that they can grow fast enough to prevail over the indigenous strains that have the ability to metabolize short chain alkanes.

Gene promoters contain specific DNA sequences and response elements that are recognized by proteins known as transcription factors. These factors bind to the promoter sequences recruiting RNA polymerase, the enzyme that copies or transcribes the gene coded for in the DNA into a messenger RNA (mRNA). The mRNA can then migrate to a ribosome where it is translated into a protein or gene product.

Gene repression and inhibition of expression refer to any process, which results in a decrease in production of a gene product, whether by a reversible or an irreversible process. A gene product can be either RNA or protein. Gene repression includes processes which decrease transcription of a gene and/or translation of mRNA. For example, a process that inhibits the formation of a transcription initiation complex or those that decrease transcription rates or those that antagonize transcriptional activation is gene repression.

An inducible promoter is one that is controlled or regulated by some extracellular factor that can increase or decrease the transcription and translation of genes into their products. In a specific example of n-alkane degradation, the alk genes of *Pseudomonas oleovorans* are responsible for the degradation of n-alkanes. These genes are located in two gene clusters that are controlled by a promoter which is controlled by the AlkS protein. This protein is responsive to the hydrocarbon octane.

The presence of octane will increase or activate the expression of these genes and their protein products. However, this same promoter is also down-regulated or repressed by the presence of a preferred carbon source such as organic acids. These bacteria would both emulsify and degrade n-alkanes unless high levels of a preferred carbon source are supplied. In this case, the genes for hydrocarbon degradation would be turned off. This would limit the usefulness of microbes in remediating hydrocarbon contaminated sites and could become less effective at degrading hydrocarbons if given more easily metabolized carbon sources. However, by inactivating the down-regulation of the promoter by preferred carbon sources, and inactivation of genes from the cluster that are needed for the metabolism of alkanes, this microbe can be engineered into an oil emulsifying bacterium that can grow on soluble carbon sources.

One means for inactivating the down-regulation by a simple soluble carbon source is to mutate the sequence of the AlkS protein that binds the carbon source in such a way as to not affect the octane binding site. Another method is to engineer the genes coding for the surfactant or bio-polymer production pathway to be under the control of a different promoter. This provides a way of controlling the production of surfactant or bio-polymer, independent of carbon source.

By maintaining growth on a medium containing a soluble carbon source, the genes that code for short chain alkane hydrocarbon metabolism can by inactivated by a number of means. Methods suitable for inactivation of these genes include, but are not limited to, chemical mutagens and UV and other forms of radiation. In addition, functional genes can be replaced by nonfunctional genes. The technology of gene silencer, developed by A. Fire et al., *Nature* 391(6669):806-11 (1998), has lead to a better understanding of how genes regulate mammalian cell function. These methods of inactivating specific genes can be used to locate key genes responsible for any metabolic process that a cell or microbe can carry out. In addition, if selected microbes for improved oil do not have completed genomic sequences available in the public domain, the entire genome can be sequenced rapidly by current technology at a fairly low cost.

One functional gene may be used to replace another functional gene. The new gene may also include a reporter gene for easy selection of microbes containing the new gene. For example, a functional cluster of genes that code for a high molecular weight hydrocarbon metabolism pathway may be inserted into a host cell. It may replace a gene cluster for lower molecular weight hydrocarbon metabolism pathway that has been removed or inactivated. In addition, the cell may be given a resistance gene for an antibiotic or other toxin. This is a commonly used method for selecting cells that have successfully incorporated new genetic material. The selected cells can then be grown to large numbers using large scale fermentation techniques known to those skilled in the art biotechnology.

However, there is a potential problem with removing the short chain alkane metabolism genes. The genes that encode for the metabolism of light chain hydrocarbons may be in clusters with the genes that are required for the production of useful metabolites such as surfactants for the emulsification of oil. Because surfactants are secreted to help the transfer of short chain alkane across the cell membrane they may be combined with the alkane metabolizing genes or controlled by the same promoter. In that case the up-regulation of useful metabolites and the down-regulation of light chain metabolism may require more complex gene manipulation. That is, key enzymes for the metabolism of short chain alkane should be inactivated not the entire gene cluster related to alkane consumption.

One problem that can prevent the success of this approach is that the genes that code for hydrocarbon emulsification of oil, which helps oil recovery, add no benefit to the microbe if the oil is not being consumed by the bacteria. Also, if the bacterial culture has a preferred carbon source in the water-flood fluid, the genes for surfactant production would quickly be lost. A microbial population will generally only carry those genes that are necessary for it to prosper in an environment. If these genes are not needed, they are soon lost. This is why the nutrients, and especially the carbon source, must be carefully controlled if the process only depends upon wild type microbes to recover oil from old wells. Therefore, some advantage must be given to the engineered microbes to make them survive better in the oil reservoir environment. The engineered microbes that can only metabolize high molecular weight oil or produce oil emulsifying surfactants must have a competitive advantage over indigenous microbes that can metabolize short chain alkanes.

It is the object of this invention to provide microbes with genes that are useful for the enhanced recovery of petroleum oil from underground reservoirs, oil sands and other sources of heavy oil while suppressing the consumption of the lighter fraction of the petroleum. In addition, it is the object of this invention to give the host or recipient organism of these genes a competitive advantage for the special environment of the hydrocarbon resource reservoir. By means known to those skilled in the art of molecular biology, genes that are isolated from bacteria and Achaea that are indigenous to oil reservoirs or naturally occurring oil seeps that provide beneficial mechanisms for enhanced oil recovery are engineered into and expressed at high levels in host microbes. The host microbes are chosen for their survival in the extreme environment of an oil reservoir. The host microbes are provided with a selective advantage for the reservoir environment. In the present invention, and in a specific case, the selective advantage is high pH tolerance. In addition, as discussed earlier, the microorganisms used in the methods of the present invention are also deficient in their ability to utilize short chain hydrocarbons but has the ability to convert hydrocarbons into fatty acids that can be useful for emulsifying the oil at alkaline pH. In addition, the engineered or modified microbes can have the ability to utilize a special energy and or carbon source that is supplied in the waterflood fluid. Genes that code for consumption of heavy oil or toxic petroleum components are also beneficial to both the microbe and oil recovery process. These beneficial genes can be preserved or transferred into the engineered microbes.

Methods designed to stop or reduce the consumption of beneficial light weight petroleum by the consortium of microbes that is used to make surfactants and other metabolites that are beneficial to enhanced oil production are described in co-pending U.S. application Ser. No. 12/869,647, published on Mar. 24, 2011 as U.S. application Publication No. 20110067856, the entire disclosure of which is expressly incorporated by reference herein. U.S. application Publication No. 20110067856 also discloses a microorganisms which, in addition to being deficient in their ability to degrade short chain hydrocarbons of about 12 carbons or less are capable of growing in an environment of high salinity, and methods and means for their selection and preparation by techniques of genetic engineering.

According to one embodiment, the consortium used in the methods of the present invention will include bacteria which additionally have the ability to live and grow in an environment of high salinity.

The technology of the present invention is implemented by inoculating an oil reservoir with a culture of one or more microbes each containing combinations of genes for the various mechanisms that are beneficial for improved oil production. The methods of the present invention allow for a wide variety of designs, and thus a combination of mechanisms may be designed for a particular type of reservoir. In addition, a means for controlling and maintaining high expression of these genes may be provided. In certain embodiments, along with the microbes, the present invention also provides the chemical component to create the right environment for the microbes that also suppresses the indigenous microbes that might consume the mobilized oil, especially the short chain alkanes.

In this example, a high pH requiring culture of microbes, are inoculated into an alkaline waterflooding fluid such as sodium bicarbonate, sodium carbonate or sodium hydroxide used to recover oil. This process is known in the petroleum industry as a method of recovering oil and is often combined with polymers and surfactants in a process known as alkaline surfactant polymer flooding (ASP). A more detailed description of this process is reported by Hsu et al. in U.S. Pat. No. 6,022,834 and is here by incorporated by reference.

Increasing the level of alkalinity in the reservoir is likely to be toxic to the indigenous microbes, but the high pH is preferred for the culture of inoculating engineered or selected microbes. In the preferred mode, the indigenous organisms, which might consume light weight oil or produce hydrogen sulfide, will be inhibited or killed. Therefore, the added nutrients will benefit only the growth of the processed-designed microbes and not the growth of detrimental indigenous microbes. In the preferred embodiment the inoculating microbes will grow rapidly at the alkaline pH of the process and produce fatty acids from the oil and other carbon sources that will emulsify the residual oil at alkaline pH. As oil is emulsified and swept away by the drive fluid, new oil surfaces are exposed to the alkaline microbes.

In addition, or as alternatives to, gene manipulation, the control of metabolic pathways within microbes can be achieved by the use of chemical compounds that affect the function of one or more enzymes in the metabolic pathways. Because it is difficult to manipulate the genetic make up of the indigenous microbes that are present in an oil reservoir at the time of inoculation with the engineered microorganisms, the metabolic pathways of the indigenous microbes are preferably controlled by chemical inhibitors, which are discussed herein below.

(1) Isolation and Selection of Oil Recovery Genes that Code for Proteins and Pathways for MEOR Over 100 oil degrading microbes have been isolated and reported. Many have been well studied and the sequences of genes related to various functions of the petroleum oil degradation process published. In some cases, for example *Alcanivorax borkumensis* SK2, the complete genome of 3,120,143 base pairs (bp) has been sequenced and published (Schneiker S et al., "Genome sequence of the ubiquitous hydrocarbon-degrading marine bacterium *Alcanivorax borkumensis*.", Nat Biotechnol, 2006 August; 24(8):997-1004) and is available from the NCBI Genome Project Database (NC_008260; GenBank AM286690). *A. borkumensis* SK2 is a marine bacterium that uses oil hydrocarbon as its exclusive source of carbon and energy. It grows on predominantly alkanes and often becomes the dominant microbe that may comprise 80% of the microbial community in an oil contaminated environment. Bacteria of the *Alcanivorax* genus belong to a larger group of hydrocarbonoclastic bacteria that also includes the genera of *Cyclolasticus, Marinobacter, Neptunomonas, Oleiphilus, Oleisprira* and *Thalassolituus*. These bacteria are able to metabolize both aliphatic and aromatic hydrocarbons. These bacteria represent a good source of genes that are involved in hydrocarbon utilization pathways.

With the advent of rapid and inexpensive genome sequencing, the bacteria's genes and their roles in hydrocarbon degradation, surfactant production and gene regulation are becoming available. Databases such as GenBank, Swiss Prot, and others provide extensive genomic sequence data from these hydrocarbon degrading microbes. This data can be searched with computer programs such as BLASTX and BLASTN at the National Center for Biotechnology Information. In addition, the use of PCR amplification based on probes with complementary sequences from the highly conserved sequences for enzymes, known to be needed for hydrocarbon degradation, can be used to isolate and characterize homologous genes from new microbes from oil contaminated sites and oil reservoirs. This can be done to analyze the change in protein sequence that has evolved to adapt to different environments. Such methods would be a useful way to find enzyme sequence modification that evolved as an adaptation to the specific environment. For example, microbes isolated from an alkaline and hydrocarbon site could contain enzymes that could degrade hydrocarbons at high pH. These enzyme sequences could be compared to homologous enzymes that function in a neutral environment to understand how to modify the sequence of proteins from neutral pH microbes to be functional in alkaliphilic microbes.

In the case of *A. borkumensis* SK2, various gene clusters have been identified that are required for; the degradation of short chain alkanes; the degradation of large alkanes up to 32 carbons in length; and the degradation of branched aliphatic and alkylcycloalkanes. Part of this process of hydrocarbon metabolism is the production of surfactants for the emulsification of various types of hydrocarbons. In the case of the smaller or lower molecular weight chain hydrocarbons, the emulsification aids in the transfer of the hydrocarbon across the cell membrane so that it can be metabolized. Therefore, this gene cluster includes genes useful for mobilization of oil which could be transferred to a host microbe. It also contains genes that are not wanted, such as genes that code for the proteins that are needed for the transfer of small alkanes into the cell for further breakdown and consumption. According to the present invention, the unwanted genes are not transferred to a host microbe or are inactivated or repressed. Genes required for the metabolism of larger alkanes, or alkylcycloalkanes, or polycyclic aromatic hydrocarbons would be candidates for transfer into host microbes.

The enzymes that oxidize short chain alkanes all the way to a fatty acid such as alcohol dehydrogenase or aldehyde dehydrogenase could be removed or modified. This pathway could be stopped at the alcohol or aldehyde or slowed down to provide short chain alcohols as co-surfactants. Alternatively, genes for the entire pathway of short chain hydrocarbons could be deleted to prevent the reduction of oil viscosity by removal of small alkanes. In the preferred mode, an obligate alkaliphile or halo-alkaliphile is engineered to serve as a host. The host alkaliphile is given the genes that are required for degradation of all the petroleum components that would be beneficial to convert into the acids and alcohols most useful for reduction of IFT and emulsification of residual reservoir oil. To compensate for the slower metabolism of these larger and more recalcitrant hydrocarbons and the lack of small fatty acid for utilization, the host microbe may also need a soluble carbon and energy source to maintain growth.

Many oil degrading microbes are useful source of genes that code for proteins to make products for the mobilization of petroleum oil. In one example, one or more bio-surfactants may be secreted by the cells to aid in the emulsification of the oil droplets so that the oil can be absorbed through the cell wall. Several strains of *Bacillus subtilis* and *Bacillus licheniformis* have been used to produce a lipopeptide named surfactin at commercial scale. This lipopeptide is also useful as an emulsifier and an antibiotic. Bacteria can be used to produce these surfactants in fermentation with manipulation of environmental and nutritional factors to increase yield as described by Cooper et al. in 1981, *Appl. Environ. Microbiol.* 42:408-412, by Javaheri et al. in 1985, *Appl. Environ. Microbiol.* 50:698-700, and Guerra-Santos et al. in 1986 *Appl. Microbial. Biotech.* 24:443-448. More recently, Mulligan et al. reported in U.S. Pat. No. 5,037,758 a genetically modified strain of *B. subtilis* ATCC #21332 with a mutation at a site in a gene of wild type *B. subtilis* that is able to produce surfactin at much higher concentrations than the wild type. Therefore, by using gene transfer techniques these well studied genes, encoding for surfactant production, can be transferred into various host cells and the production of surfactant controlled.

There are many types of bio-surfactants that could be useful in the emulsification of oil. *Pseudomonas aeruginosa* and other species can produce rhamnolipids, which have a different structure than surfactin, but still function to immobilize oil. Other surfactants, such as sophorolipid and mannosylerythritol lipid and glycolipids are produced by various strains of *Candida*. Over 200 different variations of bio-surfactants have been reported. The different surfactant structures have varying degrees of effectiveness depending on the pH, salt concentration and other environmental factors.

In addition to surfactants and bio-polymers that are functional at high pH and or high salt concentrations, the fatty acids produced from the first few steps in the biodegradation of hydrocarbons found in petroleum will serve as a surfactant at alkaline pH. Unlike the complex surfactants such as surfactin and rhamnolipids, moderate size fatty acids in the range of about 13 to 24 carbons can be synthesized directly from hydrocarbons found in petroleum with just a few extracellar enzymes. Various isolation techniques could be used to isolate alkaliphiles or alkaline tolerant microbes from high alkaline and oil contaminated site or underground aquifers. This could provide both microbes and genetic information that would be useful in selecting and engineering a culture of microbes for high pH alkaline or ASP waterflooding EOR as a combined oil recovery process.

The process of identifying new genes based on DNA sequence similarity or homology to known gene sequences of similar function is well known to those skilled in the art of molecular biology. Several methods have been used in the past. One method is to make probes of complementary RNA sequence with florescent or radio-labeled tags that will bind to mRNA of the genes being expressed by the bacteria in the environment. A second technique is to use PCR amplification of DNA isolated from the environment with probes made from conserved sequence regions of the sought after genes. A third method used for screening for bioactivities is taught by J. M. Short in U.S. Pat. No. 6,030,779. With any of these methods, new gene sequences can be isolated from environments of interest such as an oil reservoir that is currently undergoing a successful MEOR operation. An alternative is an extreme environment similar to one that might be encountered in an oil reservoir during an alkaline waterflood.

Another group of oil degrading microbes that are a good source of genes coding for useful products are microbes that can only metabolize higher molecular weight or complex hydrocarbons. For example, Banerjee et al. in U.S. Pat. No. 5,013,654 (1991) reported strains of an aerobic bacterium that will grow on paraffins of chain length longer than 12 carbons. They also isolated a mutant strain of *P. aeruginosa* SB-1, designated SB-3, which has the property of growing on solid paraffins in crude oil of 20 carbons or more, but will not grow on the liquid lighter chain hydrocarbons. Bacteria such as SB-3, which was deposited in the American Type Culture Collection, Washington D.C. as *P. aeruginosa* A.T.C.C. 39615 contain the genes for extracellular degradation and metabolism of heavy petroleum oil. These genes, and others isolated by similar means, can be transferred into a host microorganism that is able to thrive in the extreme environment of an oil well. This ability to grow in a well and degrade heavy oil, combined with the ability to produce various surfactants and biopolymers, and without the ability to consume light oil is useful in recovery of light weight petroleum. If such microorganisms could also use a simple carbon source they could grow fast and predominate the micro-flora of a reservoir. In addition, the engineered microbe could be given a toxin resistance gene in addition to alkaline tolerance as a further competitive advantage over the indigenous microbes that could consume the light weight oil.

More recently, Lei Wang et al. (PNAS Mar. 27, 2007, vol. 104 (13):5602-7) reported the genomic sequence of a thermophilic *Geobacillus* isolated from a deep oil reservoir that could grow on long chain alkanes up to C36, but was unable to grow on short chain alkanes. Their analysis of the genomic sequence showed that it did not contain any homologous gene sequences to the AlkB genes that code for the membrane bound monooxygenases that oxidize short chain alkanes. This group also reported a soluble and extracellular enzyme for the oxidation of long chain alkanes to the corresponding alcohols. This is an example of a gene that can be incorporated into a microbe for the conversion of long chain alkanes into molecules better suited to mobilize the oil into a micelle. To further convert the alcohol into a fatty acid that would have a negative charge at alkaline pH, two additional enzymes would need to be expressed by the engineered cell. The additional enzymes needed are an alcohol dehydrogenase to convert it to an aldehyde and an aldehyde dehydrogenase. Genes for these enzymes needed for long chain fatty acid production could be copied from *Geobacillus* or another microorganism such as *Mycobacterium vanbaalenii* PYR-1 or *Petrotoga* sp. AR80.

Microorganisms isolated from heavy oil reservoirs or other oil contaminated locations are likely to contain genes for all types of hydrocarbon metabolizing pathways. The membrane bound monooxygenases evolved in the transport and oxidation of light chain alkanes can be differentiated from extracellular enzymes required for the oxidation of higher molecular weight hydrocarbons which are too large and insoluble to transport across the cell membrane. If enzymes from these pathways are used in the engineered strain, then sequences modification may be required so that the enzyme are secreted and resides on the other cell membrane. Secreted enzymes must be functional in the alkaline pH and high salt concentration of the drive fluid used in ASP waterflooding.

In addition to degradation of high molecular weight paraffins, microbes may be able to degrade other unwanted hydrocarbons in petroleum oil. Polycyclic aromatic sulfur containing hydrocarbons such as thiophenes and dibenzothiophenes (DBT) can be present in petroleum at high enough levels that they are toxic to bacteria and detrimental to the refining process. The presence of sulfur compounds in oil will reduce the value of the recovered oil. The sulfur is generally removed prior to refining by expensive chemical processes. The need for a lower cost process has encouraged the development of biological processes based on several species of bacteria that have been isolated that can degrade these sulfur compounds.

In one example, Rhodococcus sp. Strain IGTS8 converts DBT to 2-hydroxybiphenyl (HBP) and inorganic sulfur. The pathway requires two monooxygenases and a desulfinase. In addition to sequence characterization, these enzymes have been improved by site directed mutagenesis to broaden the substrate specificity to include thiophenes and benzothiophenes. A more detailed description of the pathway is given by Gray, K. A. et al. in *Nature Biotechnology* 14; 1705-1709 (1996). Although this biodesulfurization of crude oil is efficient at removing sulfur with little reduction in fuel value its wide spread use has been inhibited by the cost of operating large stirred and aerated reactors. The reactor cost problem can be eliminated by transferring the genes that code for the proteins in the metabolic pathway into a host alkaliphile in such a way that they function in the higher pH of an oil reservoir undergoing alkaline waterflooding. These proteins could simultaneously degrade the sulfur containing hydrocarbons at the same time as the oil is being emulsified and swept from the reservoir during alkaline waterflood-MEOR.

An intermediate of the dibenzothiophene DBT desulfurization pathway 2-hydroxybiphenyl-2-sulfinate can be used to aid in the solubility of petroleum. Four genes in *Rhodococcus erythroplis* IGTS8 are known to code for four enzymes that catalyze each step of the desulfurization pathway. This has been used at large scale to remove sulfur from oil. Similar gene sequences have been found in more than a dozen different species of microbes including three of the genes found in *Oceanobacillus iheyensis* which is a halotolerant and alkaliphilic deep sea microorganism. *O. iheyensis* lacks the DszB gene which codes for the last enzyme that converts the sulfinate to 2-hydroxybiphenyl and sulfite or the last step in desulfurization. A pathway could be engineered to either stop at the sulfinate or the 2-hydroxybiphenyl, whichever compound was best at emulsifying the oil droplets at the reservoir's chemical and temperature conditions. In this mode, the sulfur level of the produced oil is decreased. In addition, the product of desulfurization could aid in the oil recovery as another emulsifier.

In summary, the preferred microbe of the present invention (i) contains functional genes for the extracellular modification of high molecular weight hydrocarbons at alkaline pH; (ii) lacks functional genes for the transport and oxidation of short chain alkanes at the cell membrane; (iii) contains the genes for the production of useful compounds for oil recovery and mobilization such as surfactants and polymers that are functional at alkaline pH; and (iv) is regulated to express the useful compounds at high levels even if given a simple carbon nutrient supplement. In a preferred embodiment, the microbe is capable of functioning and growing in the high pH environment of a petroleum reservoir undergoing alkaline waterflooding. Also in the preferred embodiment, the alkaliphilic microorganisms grow more vigorously on the oil at alkaline pH than the indigenous neutralphilic microorganisms. In another preferred embodiment, the microorganism is capable of functioning in either an aerobic or a limited oxygen environment. With prevention of short chain alkane degradation, the interdiction of air containing oxygen is able to speed growth and oxidative degradation of large high molecular weight hydrocarbons into smaller light weight hydrocarbons or more water miscible compounds for the reduction of oil viscosity. In addition, the petroleum's content of sulfur and nitrogen can be reduced, if desired.

(2) Selection of Extremophiles

Microorganisms that thrive in environments that would kill most organisms are referred to as extremophiles. These environments may contain organisms from all three domains although generally are almost exclusively populated by prokaryotes, many which belong to the Archaea domain of organisms. One type of extreme environment is an alkaline environment. Naturally occurring aquatics of extremely high pH have existed on the earth for many years. Current examples are soda lakes or the alkaline lakes or alkaline mineral springs, as well as some petroleum reservoirs, all of which have existed for many years at pH 9.0 or higher. This has allowed the evolution of organisms that have adapted to these consistently alkaline conditions. In addition, manmade contaminated sites, such as Lake Calumet in Illinois, have become highly alkaline after about one hundred years of industrial waste dumping. G. S. Roadcap et al. in Ground Water vol. 44, no. 4 pages 511-517, 2006 reported actively growing *Bacillus* and *Clostridia* in water up to pH 13.2. Unlike most natural soda lakes, this high pH waste site was not high in salt. A waste site of low salt concentration could provide for alkaliphile that could function at high pH but that would not require high salt concentration as well. Microbes have also developed genes coding for the resistance to these toxic or extreme environments through an evolutionary process that may have taken many millions of years. Some researchers believe that these extreme environments are more characteristic of the earth when life first began.

These extreme environments can provide sources of both microbes and their genetic information that can be transferred into the appropriate host microbes that are capable of functioning in the extreme environment of an oil reservoir. In the case where a petroleum reservoir contains indigenous microbes that are detrimental to oil recovery (light oil degraders), the pH of the waterflood fluid is adjusted to an alkaline level that is toxic to the indigenous microbes or inhibits the cell membrane enzymes needed for the up-take and metabolism of short chain alkanes. The fluid is maintained at a pH within the preferred range favorable to the engineered strain and within the preferred pH range for the secreted enzymes that can catalyze the conversion of hydrocarbons to alcohols and fatty acids. This adjustment can be by waterflooding with a fluid as part of the oil recovery process. Therefore, the selection of alkaliphilic microbes for use in oil recovery is the basis of this method. This invention provides methods of developing a culture of microbes that will carry out an oil recovery process without the unwanted consumption of short chain alkanes. In prior methods of MEOR, by simply stimulating the indigenous microbes in petroleum reservoirs, the consumption of short chain hydrocarbons could cause reduction in oil viscosity.

High pH and the combination of high pH and high salt environments can be inhabited by alkaliphilic and haloalkaliphilic microbes from both domains; bacteria and Archaea. Aquatic environments can be variable in pH or consistently high pH. Alkalitolerant (high pH tolerant) microbes can inhabit both variable and consistently high pH aquatic environments. These are different than true alkaliphilic microbes that inhabit only consistently high pH environments. Alkalitolerant microbes can function and grow over pH 9.0, but, have a preferred pH near pH 7.0.

Microbes that can live in a high pH environment often have a cytoplasmic pH higher than pH7.0, but still less than the external environmental pH. The cytoplasmic pH can be estimated by determining the pH optimum of internal cell enzymes. External enzymes either engineered into the alkaliphilic host microbe or normally found in the wild-type host alkaliphile should have a pH optimum within the range of pH used for alkaline waterflood. If the enzymes intended to convert the ranges of hydrocarbons to alcohols and fatty acids does not have a pH optimum high enough for the alkaline waterflood, then the pH optimum of the enzymes can be shifted by changes to amino acids residues on the surface of the enzyme or in the reactive site or binding sites.

Normally the proteins and other molecules that make up microbial cells will not function at a high pH. In order for enzymes and other compounds within the cytoplasm of an alkaliphile to function in the higher pH solution often found in alkaliphiles, there must be changes made to the surface of the proteins and to the pH optimum of the enzymes. Proteins can be altered in their number and type of basic amino acids that are on the surface of the protein. For example, the basic amino acid lysine is often replaced with Arginine. Analysis of the genomic sequences of these obligate alkaliphiles from both archaeal and bacterial examples indicate an increase in some amino acid residues and a decrease in other amino acid residues. A more detailed review is given by Tsuyoshi Shirai et al. in *Protein Engineering* vol. 10 no. 6 pp. 627-634, 1997 and Koki Horikoshi, *Microbiology and Molecular Biology Reviews*, December 1999, p. 735-750. And "Alkaliphiles" 1999 ISBN 90-5702-458-6 published by Kodanha Ltd Tokyo Japan, author Koki Horikoshi.

Changing one base pair of a three base pair codon is a single mutation and will not result in a charge change of the amino acid it codes for. Changing from a lysine to an aspartic acid requires a change in two bases in the codon (Lys, AAA or AAG to Asp, GAU or GAC). To make a change this radical, from a basic to acidic amino acid, requires a double or triple mutation of the codon's base pairs. These radical changes are the type found in homologous proteins as seen in the comparison of alkaliphile to non-alkaliphilic microbes. They are unlikely to occur from simple point mutations, which would not result in such large charge differences. Therefore, this type of adaptation would be slow and not likely to occur in a species for many years.

Adaptation is unlikely to occur as a result of simple horizontal gene transfer from a non-alkaliphilic microbe into an obligate alkaliphile. Genes from non-alkaliphiles or from neutral pH cytoplasm microbes must first be modified so that the enzymes they code for will have high pH optimums. This key feature of high pH cytoplasm in obligate alkaliphiles can be the basis for a means that prevents the unwanted gene transfer from most other bacteria, since most bacteria have neutral pH cytoplasms. If the indigenous microbe is not an alkaliphile, the genes from other indigenous microbes in the petroleum reservoir will not produce enzymes with the preferred pH optimum to function in an obligate alkaliphile especially enzymes that are membrane enzymes involved with the transfer and conversion of short chain alkane and aromatics. If an underground oil reservoir contained a large population of microbes that could metabolize the light weight oil, these unwanted genes could not be picked up by the engineered obligate alkaliphilic microbe. To be functional the indigenous genes would have to go though major changes so that they would be functional in the high pH cytoplasm or membrane of the alkaliphilic host microorganism. Generally, oil reservoirs that are near neutral pH would be unlikely to contain microbes that could contribute functional genes to obligate alkaliphiles.

In certain embodiments of the present invention, new genes are added to a host alkaliphilic microbe. After a microbe is selected for use in an alkaline waterflood of the reservoir, it may be desirable to add genes for the degradation and use of high molecular weight hydrocarbons and/or the production of surfactants and polymers. If these genes are transferred from other microorganisms, it may be necessary to modify the genes for high expression and function of the encoded enzymes with a high pH optimum. This can be done by a combination of rational protein sequence design and site directed mutagenesis. Therefore, the proteins and enzymes required for the production of a surfactant or a hydrocarbon cleaving enzyme useful for oil emulsification, can be engineered into an alkaliphile after the gene sequences are changed to make the proteins more functional at a pH higher than 9.0.

In accordance with the present invention, if needed, the proteins and enzymes required for the production of a surfactant or a hydrocarbon cleaving enzyme useful for oil emulsification are engineered into an alkaliphile after the gene sequences are changed to make the proteins more functional at high pH. The mutated sequences are evaluated for expression and activity at pH 9.0. In addition, the engineered microbes will not acquire the light oil consumption genes from the indigenous microbes existing in the reservoir, because the enzymes encoded for are optimal at neutral pH.

Examples of alkaliphilic microbes:
*Bacillus alcalophilus*
*Bacillus agaradhaerens*
*Bacillus cohnii*
*Bacillus vedderi*
*Bacillus firmus*
*Bacillus* strain YN-2000
*Bacillus halodurans* C-125
*Bacillus licheniformis* PWD-1
*Bacillus pseudofirmus* OF4
*Bacillus* strain A30-1 (ATCC53841) A thermophilic and alkaliphilic microbe isolated from a hot spring area of Yellowstone National Park, USA. Wang, Y. X. and B. C. Saha (1993) *J. Am. Oil Chem. Soc.*, 70, 1135-1138

*Bacillus cohnii* D-6, FERM P-1592. Produces a detergent and $H_2O_2$ resistant alkaline proteases that is also stable at 60° C. Yoshida and Horikoshi (Japanese patent JP 740710, 1972).

*Thermomonospora* sp. Isolated by George, S. P., et al. (2001) reporting a thermostable xylanase. *Bioresource Technol.*, 78, 221-224.

*Oceanobacillus iheyensis* HTE831. A halotolerant and alkaliphilic bacterium was isolated on the deep sea Iheya Ridge, Japan at 1050 meters. It is a new species not belonging to known genera.

Alkaliphilic Archaeal Halophiles:

Alkaliphilic halophiles can be found in hypersaline soda lakes such as Lake Magadi in Kenya, Wadi Natrum lakes in Egypt and soda lakes in China. These could be engineered to produce bio-surfactants and other biological oil recovery compounds that were effective at alkaline pH. Generally, alkaline pH is better for oil emulsification. Increasing the pH of the flood water can be done by adding caustic soda and would have the added advantage of suppressing the growth of endogenous microbes that might interfere or have detrimental effects on the quality of the oil produced.

*Halothermothrix orenii* is an anaerobe isolated from a Tunisian salt lake that grows in 3.4 M NaCl (20% salt) at 68 deg. C. Ref. Cayol J-L et al 1994 Int. J. Syst. Bacteriol. 44: 534-540.

*Natronobacterium magadii* and *N. gregoryi* are alkaliphilic halophiles but, not thermophiles that have been isolated from Lake Magadi in Kenya (ref. Tindall et al 1984 ATCC 43099 and 43098). They have a pH optimum of 9.5 and a salt range of 2.0-5.2 M NaCl.

*Natronomonas pharaonis* (NC_007426, NC_007427, and NC_007428), is an alkaliphilic extreme halophile isolated from a soda lake. This Archaea's 2.6 Mbp genome was completely sequenced in 2005.

*Halalkalicoccus tibetensis* (strain DS12$^T$) Isolated from Lake Zabuye, the Tibetan Plateau, China.

*Halalkalicoccus jeotgalt* B3

*Natronococcus occultus* (NCIMB2192$^T$)

*Thermococcus alcaliphilus* sp. (DSM10322) a hyperthermophilic archaeum isolated from a marine hydrothermal system at Vulcano Island, Italy. The optimum pH is 9.0 at a optimum temperature of 85° C.

In addition to the microorganisms listed above, a larger list is provided by Enache, M. et al. in the International Journal of Systematic and Evolutionary Microbiology (2007), 57:2289-229, which is expressly incorporated by reference herein. In addition to the alkaliphiles listed above, other halophiles can be selected from culture collections or isolated from high pH environments.

(3) Use of Chemical Inhibitors for Control of Metabolic Pathways

The control of metabolic pathways within microbes can be achieved by both the use of gene manipulation and the use of chemical compounds that affect the function of any enzyme in the metabolic pathway. The efficiency of oil recovery will depend on all the microorganisms growing in a reservoir that is undergoing waterflood. This might be a combination of inoculating microbes, selected or engineered microbes that have the ability to reduce the oil viscosity or emulsify the oil for higher recovery, but the process might also be affected by indigenous microbes not completely suppressed by the extreme environment created by the waterflood. The inoculating microbes can be designed to alter the crude petroleum is such a way that it more efficiently swept from the reservoir rock. The design process can be by means of gene transfer or inactivation or by the use of chemical inhibitors. Because the indigenous microbes have not been selected or modified by gene manipulation they may degrade the crude oil in such a way that it reduces the value and recoverability of the oil. This could counteract or undue the beneficial alterations brought about by the inoculating microbes. Because the indigenous microbes are already present in the underground reservoir it is difficult to transfer or manipulate their genetic makeup. Therefore the use of chemical inhibitors is the preferred method for control of the metabolic pathways of the indigenous microbes.

These chemical inhibitors can be selected or designed to bind to key enzymes known to be part of degradation pathways typically found in oil degrading microorganisms indigenous to petroleum reservoirs. FIG. 1 shows some of the key chemical reactions that are catalyzed by enzymes made by microorganisms that can utilizes hydrocarbons and the carboxylic acids made from hydrocarbons. In addition to catalyzed chemical reactions, the transfer of hydrocarbon substrate across cell membranes by transfer proteins may also be blocked by chemical compounds that bind to these transfer proteins. Chemical inhibitors can function by a number of mechanisms. Some non-limiting examples are molecules that are similar to the substrate and that compete for the reactive binding site with the substrate. These inhibitor compounds either cannot react like the substrate or if they do react they do not leave the reactive site like the intended substrate. Other types of inhibitors bind or react with the enzyme at another part of the molecule other than the reactive site and inactivate the enzyme. Inhibitors may bind strongly to the enzyme or they may react chemically with the enzyme to permanently inactivate it. Any one or a combination of these inhibitors could be used to alter the metabolic pathways of microbes involved in the utilization of crude oil.

In one non-limiting example of reaction or pathway that could be inhibited is the degradation of short chain alkanes. In general this biological degradation proceeds by absorption of the alkane by the cell membrane, conversion to an alcohol by a membrane bound enzyme followed by conversion to an aldehyde by another enzyme and then conversion to a carboxylic acid by another enzyme. If anyone of the steps is slowed down or stopped the detrimental effect of light oil consumption and the increase in oil viscosity as a result of lighter hydrocarbon loss is prevented.

In some cases the build up and secretion of the intermediates in the pathway could also benefit the recovery of oil. For example, short chain fatty alcohols in the size range of 2 to 8 carbons are useful as co-surfactants in emulsifying oil. In another example, slightly larger size fatty acids in the range of 6 to 20 carbons are useful at emulsifying oil especially at alkaline pH by forming soap molecules that help for micelles of oil. In the above examples, a buildup of alcohol could be induced by the addition of an inhibitor of the enzyme alcohol dehydrogenase of short chain fatty. A buildup of fatty acids could be achieved by inhibiting anyone of the enzymes required for the beta-oxidation of fatty acids.

A number of chemical compounds have been reported to inhibit the beta-oxidation of fatty acids. Thijsse GJE. in 1964 reported fatty acid accumulation in alkane-oxidizing *Pseudomonas* (Biochim. Biophys. Acta 84:195-197). In 1979 B. M. Raaka and J. M. Lowenstein reported that DL-2-bromooctanoate causes complete and irreversible inactivation of 3-ketothiolase I a beta-oxidation enzyme (J. of Biological Chemistry Vol. 254, No. 14, pp. 6755-6762). Salicylic acid was also reported to inhibit 3-ketoacyl-CoA thiolase in *P. fluorescens* by M. H. Choi et al. in 2008 published online Oct. 3, 2008 (DOI 10.1002/bit.22149). The beta-oxidation inhibition was comparable to that with acrylic acid and was believed to be similar but with the added advantage that salicylic acid was not metabolized by the microbe as is acrylic acid and would therefore be longer lasting.

Because of medical importance fatty acids to humans, the inhibition of fatty acid transfer across cell membranes has been more studied in eukaryotic cells than in bacteria. At least six of the mammalian fatty acid transfer protein genes have been cloned and their proteins characterized (Wu, Q.; Ortegon, A. M.; Tsang, B.; Doege, H.; Feingold, K. R.; Stahl, A. Mol. Cell. Biol. 2006, Vol. 26, pp. 3455-3467). The identification of small compound inhibitors has been a key technology for the development of treatments for obesity, cardiovascular disease and fat-induced insulin resistance. High-throughput screening for fatty acid uptake inhibitors in humanized yeast is described by P. N. Black and C. C. DiRusso in U.S. Pat. No. 7,070,944. Fatty acid transfer proteins are also found in bacteria and a report on a family of fatty acid transporters conserved from bacteria to humans is given by Hirsch, D.; Stahl, A.; Lodish, H. F.; Proc. Natl. Acad. Sci. USA, 1998, Vol. 95, pp. 8625-8629.

More recent work has utilized transposon-induced mutants of bacteria of the genus Alcanivorax to identify genes required for the export of fatty acid derivatives such as wax esters and polyhydroxyalkanoic acids (PHA). A recent report is given by E. Manilla-Perez et al. was published in J. Bacteriology Vol. 192 No. 3 (2009) pp. 643-656. The export of fatty acids would be beneficial for increasing the acid number of crude oil for emulsification and the import of short chain hydrocarbons would be beneficial to inhibit to prevent depletion of light oil from the reservoir petroleum. Isolating the genes that code for each transfer protein would provide a method of screening for inhibitors that do not decrease export of fatty acids, but that inhibit the import of short chain alkanes or other light hydrocarbons.

Combination of genetic manipulation and use of chemical inhibitors such as acrylic acid has been used for production of polyhydroxyalkanoic acids (PHA) because of their use to produce biodegradable thermoplastics and elastomers. A more detail report of PHA production by recombinant *E. coli* in combination with the use of acrylic acid inhibitor is given by K. Zhao et al. in FEMS Microbiology letters 218 (2003) pp. 59-64. More recent work has focused on the use of microbes that are able to secrete the fatty acid derivatives such as *Alcanivorax borkumensis*. A recent report is given by E. Manilla-Perez et al. was published in J. Bacteriology Vol. 192 No. 3 (2009) pp. 643-656.

The effectiveness of any chemical inhibitor can be determined by testing a range of inhibitor concentrations added to a culture of microorganisms growing on a sample of crude petroleum or a simple hydrocarbon substrate such as hexadecane. The secretion of fatty acids into the medium can be determined by conversion of the fatty acid to a methyl ester for analysis by GC. In example 4a digestion of oil from the Red River formation in Montana was used to test a few different chemical inhibitors of beta-oxidation to measure the inhibitors affect on oil and the acid content of crude oil.

Further details of the invention are provided in the following non-limiting examples.

All references cited throughout this disclosure and the references cited therein are expressly incorporated by reference herein.

Example 1

Figure 4:
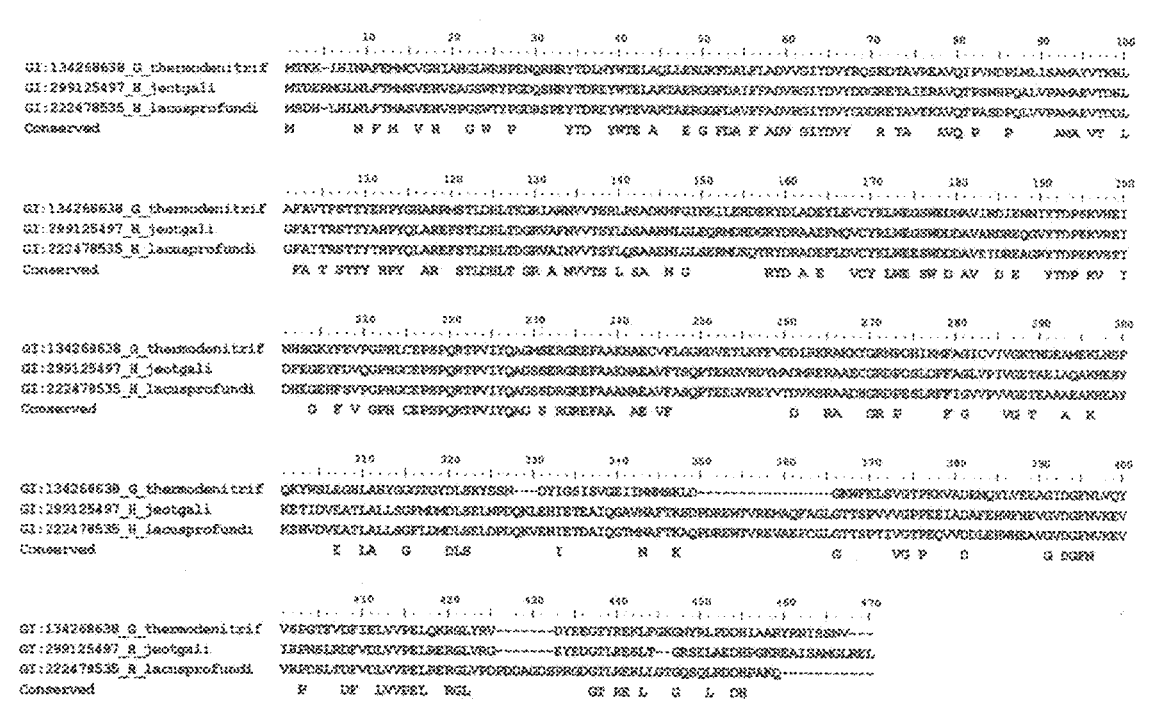

FIG. 4 shows the alignment of the amino acid sequences of the LadA long chain alkane monooxygenase (SEQ ID NO: 1) with the hypothetical protein Gen ID 9420269 HacjB3_12265 from *Halalkalicoccus jeotgali* B3 alkalitolerant halophiles (SEQ ID NO: 2) and with another hypothetical protein from the halophile, *Halorubrum lacusprofundi* (ATCC 49239) Gene ID 7401614 Hlac 0096 (SEQ ID NO: 3). The amino acid compositions for the three proteins are shown below.

Protein: GI: 134268638_G_thermodenitrificans
Length=440 amino acids
Molecular Weight=50463.66 Daltons

| Amino Acid | | Number | Mol % |
|---|---|---|---|
| Ala | A | 28 | 6.36 |
| Cys | C | 5 | 1.14 |
| Asp | D | 28 | 6.36 |
| Glu | E | 32 | 7.27 |
| Phe | F | 18 | 4.09 |
| Gly | G | 33 | 7.50 |
| His | H | 20 | 4.55 |
| Ile | I | 26 | 5.91 |
| Lys | K | 31 | 7.05 |
| Leu | L | 33 | 7.50 |
| Met | M | 10 | 2.27 |
| Asn | N | 20 | 4.55 |
| Pro | P | 16 | 3.64 |
| Gln | Q | 10 | 2.27 |
| Arg | R | 23 | 5.23 |
| Ser | S | 23 | 5.23 |
| Thr | T | 19 | 4.32 |

-continued

| Amino Acid | | Number | Mol % |
|---|---|---|---|
| Val | V | 32 | 7.27 |
| Trp | W | 7 | 1.59 |
| Tyr | Y | 26 | 5.91 |

Protein: GI: 299125497_H_jeotgali
Length=461 amino acids
Molecular Weight=51901.50 Daltons

| Amino Acid | | Number | Mol % |
|---|---|---|---|
| Ala | A | 44 | 9.54 |
| Cys | C | 3 | 0.65 |
| Asp | D | 39 | 8.46 |
| Glu | E | 49 | 10.63 |
| Phe | F | 21 | 4.56 |
| Gly | G | 35 | 7.59 |
| His | H | 13 | 2.82 |
| Ile | I | 14 | 3.04 |
| Lys | K | 9 | 1.95 |
| Leu | L | 30 | 6.51 |
| Met | M | 12 | 2.60 |
| Asn | N | 10 | 2.17 |
| Pro | P | 21 | 4.56 |
| Gln | Q | 15 | 3.25 |
| Arg | R | 38 | 8.24 |
| Ser | S | 24 | 5.21 |
| Thr | T | 28 | 6.07 |
| Val | V | 34 | 7.38 |
| Trp | W | 6 | 1.30 |
| Tyr | Y | 16 | 3.47 |

Protein: GI: 222478535_H_lacusprofundi
Length=458 amino acids
Molecular Weight=50806.91 Daltons

| Amino Acid | | Number | Mol % |
|---|---|---|---|
| Ala | A | 41 | 8.95 |
| Cys | C | 3 | 0.66 |
| Asp | D | 47 | 10.26 |
| Glu | E | 44 | 9.61 |
| Phe | F | 17 | 3.71 |
| Gly | G | 32 | 6.99 |
| His | H | 15 | 3.28 |
| Ile | I | 10 | 2.18 |
| Lys | K | 11 | 2.40 |
| Leu | L | 30 | 6.55 |
| Met | M | 6 | 1.31 |
| Asn | N | 6 | 1.31 |
| Pro | P | 26 | 5.68 |
| Gln | Q | 15 | 3.28 |
| Arg | R | 30 | 6.55 |
| Ser | S | 27 | 5.90 |
| Thr | T | 34 | 7.42 |
| Val | V | 44 | 9.61 |
| Trp | W | 6 | 1.31 |
| Tyr | Y | 14 | 3.06 |

Example 2

Isolation of Microbes from High pH and High Salt Site and Isolation from High pH and Low Salt Sites Step 1: The Isolation of Microbes from High pH Environments The isolation of microbes from high pH and high salt sites, or the isolation from high pH and low salt sites is a preferred method of obtaining host microorganism for an alkaline oil recovery process. Sites that have been contaminated with petroleum oil for a long time are most preferred because they may also contain microbes that can grow on a variety of hydrocarbons. Some oil wells contain water that is of high pH and has been at high pH for many years. Microbes from alkaline petroleum sites are also likely to be resistant to the toxic effects of petroleum and could be used for oil recovery or as host microorganisms for engineering metabolic pathways useful for oil recovery. The microorganisms isolated from these types of sites are also useful as a source of protein sequences of enzymes that are optimized for high pH function.

Alkaline environments of consistently high pH that are also high in sodium ion concentrations (salinities exceeding 100,000 ppm total dissolved solids) are the most common. Soda lakes and soda deserts are stable and naturally occurring environments found worldwide. These are the best for isolation of alkaliphilic and halophilic microorganisms. Environments that have variable pH and salt concentrations are more likely to contain alkali-tolerant and halo-tolerant microorganisms. Alkaline sites containing liquid hydrocarbons, such as petroleum oil fields or waste oil/brine disposal pits or evaporation ponds are good sites for isolation of microbes that are alkaliphiles or halo-alkaliphiles and also have the ability to metabolize various types of hydrocarbons. Groundwater high in calcium ions at high pH is less common, but is a good source of alkaliphiles that are not also halophiles and can grow in low concentrations of salinity.

Microbes selected for use in MEOR may be required to function in the low oxygen environment of an oil well. Facultative anaerobes are ideal host microorganisms because they can survive exposure to oxygen. Especially good are microbes that can use nitrate as an election acceptor. Aerobic microbes may be used in applications where large amounts of air can be injected with the waterflood fluid. Microbes isolated from these environments can also be a source of genes or gene sequence information that can be used to genetically modify a microbe or engineer a microbe to be tested and used on oil reservoirs of high pH or where an alkaline brine is used as waterflood.

In one example, H. Al-Awadhi, et al., in *Appl. Microbiol. Biotechnol.* 2007, 77:183-186, reported the isolation of the strains; *Marinobacter, Micrococcus, Dietzia, Bacillus, Oceanobacillus*, and *Citricoccus* that were able to grow on a range of alkanes and aromatic compounds as sole carbon and energy sources. These microbes were isolated from the intertidal zone of the Arabian Gulf coast. Petroleum oil pollution is acute in an oil-producing area such as the Arabian Gulf. The long coastline of the Gulf comprises areas in which tidal water is trapped and becomes saline and alkaline as a result of evaporation. Therefore sites containing both oil and high salinity at alkaline pH are likely to contain alkaline microbes that can utilize various hydrocarbons.

Following the method used by Al-Awadhi et al., microbes in biofilms coating gravel particles are scraped off with a sterile toothbrush into sterile water. A count of alkaliphilic oil-utilizing microbes is made by growth on an inorganic agar medium described by Horikoshi 1998, Alkaliphiles. In: Horikoshi K, Grant WD (eds) Extremophiles: microbial life in the extreme environments. Wiley-Liss, London, pp 155-179. The halophiles were counted on inorganic medium described by Sorkhoh et al. (1990). Representative colonies were isolated and purified on the above solid media. The pure cultures were identified by analyzing their genomic deoxyribonucleic acid (DNA) sequences. Genomic DNA was extracted by a DNA extraction kit (Sigma, USA). The 16S ribosomal ribonucleic acid (rRNA) was amplified by polymerase chain reaction (PCR). The 550-bp fragment of the 16S ribosomal DNA was enzymatically amplified with the universal eubacterial primer combination GM % F with the sequence 5'-CCTACGGGAG-GCAGCAG-3' (SEQ ID NO: 4) and DS907R with the sequence 5'-CCCCGTCAATTCMTTTGAGTTT-3' (SEQ ID NO: 5) (Santegoeds et al. 1998 Appl. Environ Microbiol 64:3731-3739). The PCR products were purified and sequenced. Sequences obtained were compared to those of known bacteria via the GenBank database and deposited under the accession number DQ646492-DQ646515.

The isolates were surveyed for growth on medium containing 0.5% of individual hydrocarbons alkanes from C-13 to C-40 and the aromatic compounds naphthalene and phenanthrene as sole carbon sources. The pH of the medium for the alkaliphiles was maintained at pH 11. It was found that the optimum pH for growth of oil-utilizing alkaliphilic isolates was between pH 8 and pH 10. All isolates could tolerate alkalinity up to pH 11 but not pH 12.

Al-Awadhi et al. found that most of the isolates could utilize a wide range of alkanes from C-13 to C-40 and the two aromatic hydrocarbons tested. However, a few could only utilize a narrow range of hydrocarbons. This method could be used to isolate alkaliphilic wild type microbes that only had the ability to degrade high molecular weight hydrocarbons. By these methods, pure strains could be obtained of halophilic and alkaliphilic microbes that could degrade only certain target ranges or types of hydrocarbons. Alternatively these isolate strains could be sequenced to find variations in enzymes that are known to degrade certain size ranges of hydrocarbons, such as the monooxygenase LadA, which is an enzyme that converts alkanes longer than 15 carbons to alcohols, or NidA3B3 that is a degrading enzyme of polycyclic aromatic hydrocarbons. The sequence information could be used for adapting other enzymes for function at high pH or salinity by homologous amino acid replacement.

Less is known about the microorganisms found in environments that are low in salinity, but high in alkalinity and calcium. The microbial communities may not develop as well because of the lower concentration of nitrogen and phosphorous. Industrial waste water ponds, such as sites of cement and indigo production, are good sites to explore for low salt alkaliphiles. G. S. Roadcap et al. Ground Water 44, No. 4:511-517 (2006) reported finding more than 100 strains of *Bacillus* and *Clostridium* by microbial 16S ribosomal RNA sequencing from a high pH and low sodium ground water site at Lake Calumet, near Chicago Ill. The pH of the water from this site is over 13. The Lake Calumet site is also known to have hydrocarbon contamination and is likely to contain hydrocarbon degrading microbes that are also able to grow at high pH. By using a procedure similar to Al-Awadhi et al. with a medium low in sodium, strains of microorganisms could be isolated from a site such as the Lake Calumet site. Those microbial isolates could be tested for the ability to utilize either light or heavy hydrocarbons.

Step 2: Isolation of DNA and Genes Needed for Surfactant Production and Liquid Oil Consumption Microbial strains selected for high and effective surfactant production can be further characterized by gene sequencing. DNA is extracted from poly-carbonate filters as described by Minz et al. (1999) *Appl. Environ. Microbiol.* 65: 4666-4671. This procedure was modified by Kebbouche-Gana et al. The DNA was electrophoresed, excised from the gel and purified with a gel extraction kit (Genomic DNA purification system PROM, EGA). Purified DNA from selected strains are amplified with specific 16s rRNA archaeal primers (5'-TTCCGGT-TGATCCYGCCGGA-3'(SEQ ID NO: 6) and 5' YCCG- GCGTTGAMTCCAATT-3' (SEQ ID NO: 7)). 16s rRNA sequence information can be aligned with rRNA sequence from known alkaliphiles for genera and family identification.

DNA or mRNA probes can be based on known genes from an organism that produces a surfactant. One example is *Pseudomonas aeruginosa*, which produces rhamnolipid. The synthesis of this glycolipid is by sequential glycosyl transfer reactions. The genes involved in rhamnolipid biosynthesis are encoded on a plasmid, and their expression is regulated by a quorum sensing system. A more complete review is given in Lang and Wullbrandt (1999) *Appl. Microbiol. Biotechnol.* 51:22-32. Other species, such as *Bacillus subtilis*, produce surfactin, a lipopeptide which contains about 7 amino acid residues. Other microorganisms secrete higher molecular weight biosurfactants consisting of polysaccharides, lipoproteins, and lipopolysaccharides. Isolation and identification of the surfactants secreted by the isolated strains can be done by HPLC with a mass-spec detection system. Identification of the chemical nature of the surfactants produced by each isolated strain can be useful information for finding genes that are required for the surfactant production and secretion. For example, a glycolipid similar to rhamnolipid would likely be dependent on genes similar to those involved in its biosynthesis in *P. aeruginosa*. These genes from well characterized microbes could be used to construct probes for finding similar genes in the alkaliphilic isolates.

However, if the surfactants produced by the alkaliphilic microbes are totally new and unlike any other well-studied surface active compounds, then other methods of gene isolation can be used. For example, correlating higher levels of specific mRNAs with production of high levels of surfactant can be used to find needed genes. If the presence of alkanes induces the production of surfactant, then the level of mRNA needed for surfactant production will be increased. The use of DNA microarrays can identify the increase in gene transcription to mRNA when surfactant production is induced, as can whole transcriptome shotgun sequencing of RNA or cDNA (WTSS or RNA-Seq). Also, sequencing of the specific cDNA, made from the increased mRNA can be used to identify the required genes sequences.

Based on this method, the identification of genes required for the production of surfactant and the degradation of liquid oil can be done by mRNA differential display. This method was used to identify Cyclohexonone metabolism related genes (Brzostowicz et al. (2000) *J. bacterial.* 182: 4241-4248). These mRNA techniques make it possible to access regulated genes directly without purification of gene products. These approaches are based on comparisons of two cultures and the identification of genes whose mRNA is more abundant when a metabolic pathway is induced. In the above example, if surfactant production is induced by the presence of oil, then mRNA that codes for surfactant production as well as enzymes for oil metabolism will be at higher levels compared to the uninduced culture. These techniques rely on the hybridization of DNA on membranes as described by Chuang and Blattner 1993 *J. bacteriol.* 175: 5242-5252. It was by this method that Brzostowiez et al. that led to the discovery of the genes for two monooxygenase enzymes responsible for the oxidation of cyclohexanone. This same technique can be used for the identification of genes coding for proteins and gene products of alkaliphilic microbes that lack enough sequence homology to bind to probes constructed based on protein sequence mesophilic homologous enzymes.

Probes may also be based on protein sequence of homologous enzymes with highly conserved catalytic site and binding sites. In this case a short degenerate DNA probe is constructed to bind with any DNA that had the sequence of base pairs that would code for the highly conserved amino acid residue sequence.

Although all these methods can be successful at isolating new genes required for surfactant production and liquid hydrocarbon oil degradation in halophiles, genome sequencing of larger numbers of obligate halophiles will enable faster identification and isolation of new genes.

Step 3: The Prevention and Modification of Short Chain Alkane Metabolism

The expression of genes required for the production and secretion of surfactants and for the degradation of high molecular weight hydrocarbons are beneficial to the mobilization of oil. Degradation of short chain alkanes and other low viscosity petroleum components is very detrimental to oil recovery. Therefore, if the genes of a microbe could be modified so that the microbe does not metabolize light oil, the viscosity would decrease and the recovery of petroleum would increase. However, this must be done in such a way that production of surfactant, which may be under the control of a single gene promoter, is not also prevented. With the loss of liquid oil metabolism, another utilizable carbon source is needed to offset the loss of energy from the light chain hydrocarbon metabolism. Often the genes needed for both liquid hydrocarbon consumption and surfactant production are clustered together. Therefore, deactivating or removing the genes needed for short chain alkane uptake must be done in such a way that the genes needed for high production of surfactant are not deactivated or down regulated.

One method of achieving this specific gene modification is by homologous gene replacement. A wild type gene is replaced with a new gene that has a modified nucleotide sequence and that codes for a protein with a different amino acid sequence. This process can be used to make small changes to enzymes to change the catalytic efficiency or specificity of the enzyme. A change of one or two amino acid residues can disable the ability of the new enzyme to bind the same substrate or to catalyze key steps in the conversion of substrate to product at the same rate. This process has been used in many genetic systems wherein similar genes are replaced by a mutated gene by homologous recombination (Molecular Biotechnology edited by Glick and Pasternak, 2003, Chapter 8). Along with the mutated gene, a selectable maker is also incorporated so that new microbes that have taken up the mutated gene can be selected. This process requires a certain level of genetic manipulation tools. Fortunately, a gene knockout system has been developed for the halophilic *Archaea, Haloferax volcanii* and *Halobacterium salinarum* based on the pyrE gene reported by Bitin-Banin et al. in *J. Bacteriol.* 2003, 185: 772-778. This system has been further developed, and now four different selection principles are available (Allers et al. *Appl. Environ. Microbiol.* 2004, 70: 943-953) for *Hf. volcanii*. By using this technique or similar gene replacement techniques with selectable makers, the monooxygenase genes isolated from the wild type halophiles can be replaced with modified gene sequences.

By this process or other genetic manipulation processes, a number of changes can be made in the amino acid sequences of enzymes that facilitate the uptake or metabolism of light chain alkanes. This process can be done by random changes to any amino acid in the enzymes sequence, by trial and error. The resultant enzymes with the amino acid changes can be tested for changes in substrate binding, substrate specificity, and rate of conversion to product. In general, most of the random changes will have little effect, or will decrease the catalytic rate. This process is much easier if the three dimensional structure of the enzyme is known or can be determined by X-ray crystallographic analysis. In this example the structure of some alkarie specific monooxygenases have been determined and would be useful in predicting key amino acids to change. For example, by making point mutations of the amino acid residues at the binding sites also known as histidine boxes, it would likely prevent or cause a reduction in the rate of alkane metabolism.

Changing any of the amino acid residues, especially the histidines, will affect the ability of these enzymes to metabolize liquid hydrocarbons. A number of these modified enzymes can be evaluated in a model alkaliphilic host, such as *Oceanobacillus iheyensis*, to determine the enzymes ability to function at high pH. Modified wild type alkaliphiles with the mutated alkane conversion enzymes can be evaluated at the laboratory scale for their ability to produce surfactant, but with limited ability to grow on octane or diesel as a carbon source. From the group of engineered microbes, the strains that achieve high levels of growth utilizing an inexpensive carbon source, and that produce high levels of surfactant, and that consume the smallest amount of light molecular weight oil (C6-C8) are selected. The consumption of short chain alkane can be determined by analysis of remaining oil in the reaction vessel. A more sensitive method is with a carbon-14 isotope labeled alkane. Small amounts of uptake of the isotopic carbon can be measured in the cells. Alternatively, the rate can be determined from the isotopic carbon dioxide produced.

From this group of engineered microbes the selected halophiles are tested for their ability to mobilize oil in a laboratory scale waterflood core sample test. This test consists of saturating a reservoir rock core sample or a packed sand column with petroleum oil. A flow of water or brine is then pumped through the core sample until the free oil is washed out. Then the microbe culture in a growth buffer is introduced into the core sample that still contains the residual oil. The core sample inoculated with microbes is left to incubate for one to two weeks. After incubation, a flow of waterflood buffer is passed through the core and the amount of oil removed by this flow is measured as a function of buffer flow volume. With this small scale laboratory test, the effectiveness of each of the engineered and wild type cultures can be measured and compared. The improved cultures should show an increase in the rate and total amount of oil removed from the core. There should also be an increase in the number of microbes, indicating growth in the high salt environment. However, this short test does not indicate oil or light chain alkane consumption because the time that the microbes are in contact with the petroleum is too short and there is no easy way to measure the total remaining oil.

Therefore, another test is needed to determine the short chain alkane consumption. The conditions of the digestion should match the waterflood drive buffer or fluid. It should contain the soluble carbon source, such as molasses, that will be used to supplement growth. However, the soluble carbon source should not be a catabolite that will cause repression of alkane degradation pathway genes. A report of carbon sources that can cause repression of alkane degradation pathways in *Pseudomonas putida* is given by F. Rojo et al. in the *J. Bacteriology* 2003 185: 4772-4778. The incubation should be long enough (several weeks) to measure degradation and loss of alkanes or a change in total alkane hydrocarbon composition or a change to the relative amount of various hydrocarbons if a mixture or sample of petroleum oil is used. The measure of an engineered or selected microbe that will be a good commercial candidate is that there is no decrease, or relative small decrease, in the lighter weight hydrocarbon. As a comparison, this same test is performed with the indigenous microbes isolated from the location or oil reservoir. A test using only the stimulation of indigenous microbes might produce less oil, or produce oil with a larger high molecular weight fraction. The best cultures will be the ones that can produce the most surfactant and the most oil without decreasing the percentage of light weight oil in the petroleum samples.

Example 3

Addition of Fatty Acids of Various Length Alkanes to Crude Petroleum Oil to Experimentally Determine the Emulsification of Oil at Alkaline pH This test was done by mixing small amounts of carboxylic acids with a petroleum sample. The petroleum sample used was a sour oil from the Sleep formation of Pennsylvanian sandstone in Byron, Wyo. The carboxylic acids used in this test were; a 16 carbon (hexadecanoic) acid $C_{16}H_{32}O_2$, an 8 carbon (octanoic) acid $C_8H_{16}O_2$, a 4 carbon (butanoic) acid $C_4H_8O_2$, a three carbon acid $C_3H_6O_2$ and a 2 carbon acid $C_2H_4O_2$. The amount of acid added was approximately enough to neutralize 1.0 mg of KOH per gram of oil or an acid number of about 1.0. The organic acid and oil were heated to about 50° C. for 30 minutes to dissolve the acid in the oil. The oil was then mixed with the sand at the ratio 3 ml (2.67 g) oil with 10 g sand. The sand was 30 mesh play sand from Home Depot. The oil and sand mix were packed into a small column and then eluted with the test drive fluid by gravity flow. All test elutions were done at a room temperature of about 25° C. The elution volume was 20 ml, the oil and aqueous fluid were separated and the dried oil was weighted. The first elution was with a 1% NaCl brine solution at neutral pH. The second elution was with a 0.05% NaOH, 1% NaCl brine solution at about pH12. And the third elution was a 0.05% NaOH, 1% NaCl, 1% Tween 20 brine at pH 12. The first elution was to test a waterflood with brine. The second was to test an alkaline waterflood and the third elution was to represent an alkaline waterflood with chemical surfactant. The results indicate that the additional oil elution at alkaline pH was affected by the chain length of the fatty acid. The longer fatty acids have increased the viscosity of the oil and decreased the elution from sand, which had more impact than the soap of the fatty acid help the emulsification of the oil. The shorter chain length fatty acid may have been less soluble in the oil and more soluble in the water and not been as effective at emulsifying the oil with the brine. This effect is temperature dependant and the elution experiment should be done at approximately the same temperature as is expected within the reservoir formation. This is also done to better determine the preferred size range for the microbially produced fatty acids from the degradation of the reservoir crude oil.

A similar small scale test can be done with the partially bio-degraded crude oil. The modified oil can be extracted with a standard concentration of sodium hydroxide and then back titrated to determine the amount of extractable fatty acids. The extracted fatty acids can be determined by conversion to methyl esters for GC analysis. In addition, sand pack columns can be used to evaluate the alkaline elution of the partly degraded oil. The degree of biodegradation of the oil can be evaluated by a combination of acid number, fatty acid type, GC analysis of degraded and undegraded oil and oil recovery from sand pack columns. The preferred microbes are the cultures that can increase the acid number and the type of acids that are best for higher oil elution under alkaline flooding and that do the least degradation of the shorter chain hydrocarbons.

TABLE 1

Results for sand pack column elution
Recovered oil (gram) from 10 g sand/3 mL (2.67 g) Byron column

|  | Control | 1.25 mg C2 | 1.875 mg C3 | 2.5 mg C4 | 5 mg C8 | 10 mg C16 |
|---|---|---|---|---|---|---|
| 1% NaCl | 1.14 | 1.12 | 1.07 | 1.16 | 1.10 | 1.05 |
| 1% NaCl/0.05% NaOH | 0.24 | 0.09 | 0.20 | 0.33 | 0.46 | 0.17 |
| 1% NaCl/0.05% NaOH/1% Tween | 0.17 | 0.14 | 0.28 | 0.37 | 0.23 | 0.02 |
| Total recovered oil (g) | 1.55 | 1.35 | 1.55 | 1.86 | 1.79 | 1.24 |

Example 4

Deletion of Genes in the Alkane and Fatty Acid Degradation Pathway of *Haloferax volcanii*

The acyl coenzyme A dehydrogenase protein, encoded by the fadE gene, has been shown in *E. coli* to be necessary for efficient degradation of fatty acids via the beta-oxidation pathway. In the alkane degrading strain *Geobacillus thermoleovorans* B23, the fatty aldehyde dehydrogenase protein, AldH, was identified and shown to convert various fatty aldehydes to fatty acids. Similarly, a fatty aldehyde dehydrogenase encoded by ald1 in *Acinetobacter* sp. strain M-1 was shown to convert various fatty aldehydes to fatty acids.

Searches of FadE, Aldh, and Ald1 were carried out in the Genbank database, using BLASTP, to find matches in the genome sequence of *Haloferax volcanii* DS2. The best match for FadE consisted of Acd3 (YP_003535250.1). The best match for both AldH and Ald1 was AldY5 (YP_003533953.1).

Figure 5:
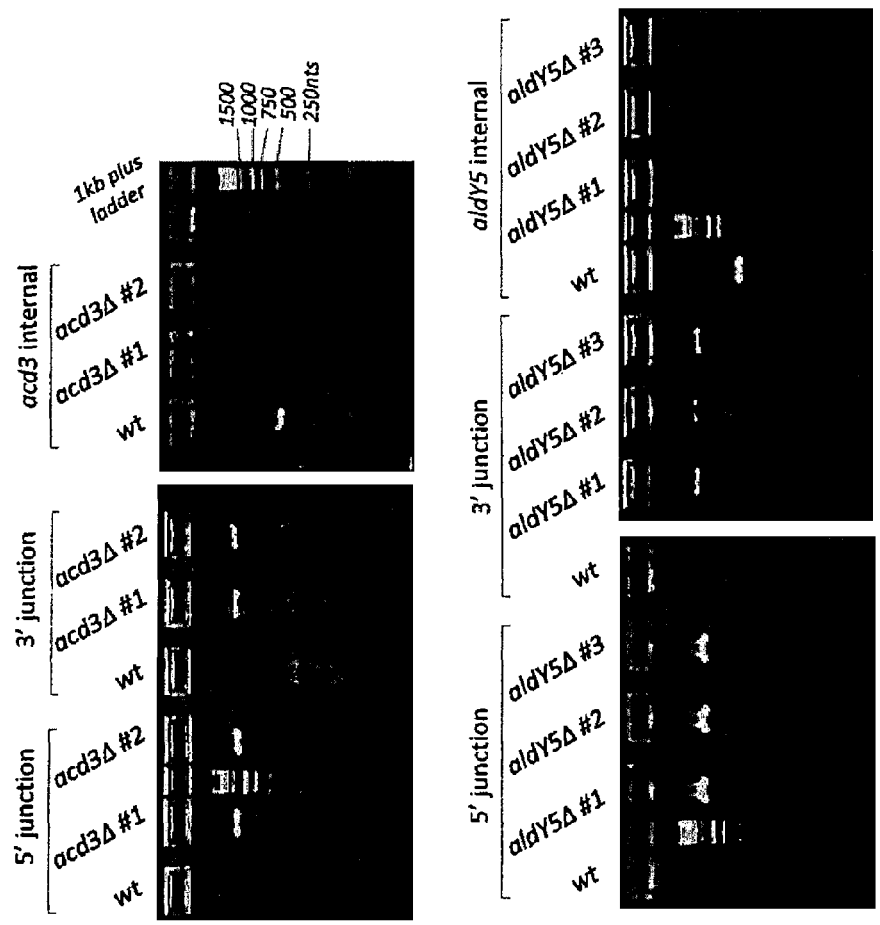
FIG. 5 Generation of acd3 and aldY5 gene knock outs of *Haloferax volcanii* DS2. The 1.3 kilobase PCR band generated from the genomes of multiple mutant isolates, but not from that of wildtype *Haloferax volcanii*, demonstrates successful acd3 and aldY5 gene knock outs.

Directed gene knockouts were made in the acd3 and aldY5 genes by homologous recombination in strain GFF127, an isolate of *Haloferax volcanii* DS2 containing a knockout of the pyrE2 gene with a mevinolin resistance marker (i.e., pyrE2Δ:MEV). For gene knockouts, linear DNA segments were constructed containing 1000 nucleotides of sequence immediately upstream of the target gene, followed by the *Haloferax volcanii* pyrE2 gene, followed by 1000 nucleotides of sequence immediately downstream of the target gene. The DNA segments were generated by a fusion PCR strategy, whereby the three parts of a segment (target gene flanks and pyrE2 gene) were PCR amplified in a first step, separately, from the *Haloferax volcanii* genome. PCR primers for amplification of the pyrE2 gene at the upstream and downstream ends contained sequences at the 5' ends that matched the upstream and downstream flanking sequences of the gene targeted for knockout. In a subsequent step, the three parts of the segment were assembled in a PCR reaction that contained the three parts and PCR primers at either end of the entire segment. DNA segments were then transformed into GFF127 by PEG transformation (Dyall-Smith, The Halohandbook: protocols for haloarchaeal genetics, 2009) and the pyrE2 gene was selected on medium lacking uracil (Hv-Ca medium). Transformant colonies were streaked for isolation. Replacement of the target genes was confirmed by PCR amplification across junctions at both ends at sites of integration, using a primer internal to the pyrE2 marker and a primer external to the integration construct, approximately 1.2 kb upstream or downstream. The approximately 1.3 kilobase PCR band generated from the genomes of multiple mutant isolates, but not from that of wildtype *Haloferax volcanii*, demonstrated successful acd3 and aldY5 gene knock outs (see, FIG. 5). Absence of the target gene in the genomes of mutant isolates was confirmed by the absence of a PCR product generated using a pair of DNA primers internal to the gene (491 or 480 base pairs for the acd3 and aldY5 genes, respectively); as a control, the internal PCR product was observed when the PCR was carried out in parallel with a wildtype strain.

Example 5

Determination of the Effect of Chemical Inhibitors for Increasing the Acid Content of Oil Experimental Procedure:

An oil degrading microorganism was used to evaluate the use of chemical inhibitors to slow the utilization of hydrocarbons in petroleum. In a non-limiting example, three different chemical compounds that have been reported to inhibit beta-oxidation were tested in oil and culture medium on a petroleum sample with a strain of *Rhodococcus rhodochrous* ATCC #53968 in m9 minimal medium. To test the ability of each chemical inhibitor to slow the consumption of fatty acids a culture of bacteria was grown on a crude oil sample for a period of three days with crude petroleum oil as the only carbon source. Four separate flasks were set up, each with an oil to aqueous media ratio of 1 to 5 (10 ml of crude oil to 50 ml of culture medium). Each of the three chemical inhibitors was added to a separate flask and a fourth flask was allowed to digest without the addition of a chemical inhibitor as a control. The flasks were shaken at a room temperature of about 25° C. under aerobic conditions. The progress of the microbial digestion was monitored by the optical density at 600 nm and by visual inspection of the brown oil color in the aqueous phase. Three days after the addition of inhibitors, or a total of six days of incubation with oil, a small sample of oil (0.31 g) was removed. A second sample of the same size was remover after another 6 days. The organic acids were extracted from each oil sample with 1% NaOH in 70% ethanol. The samples were shaken vigorously for one minute. The aqueous extract material was then extracted with hexane to remove any trace of oil. The samples of extracted organic acids were then dried under vacuum and converted to methyl esters with $BF_3$ in methanol.

The mixtures of methyl esters were analyzed by GC (gas chromatography) using a HP (Hewlett Packard) 5890 GC with an Agilent Technologies capillary column, HP-5 (crosslinked 5% PH) ME Siloxane 0.25 micrometer coating with a length of 30 meter and a column ID (internal diameter) of 0.32 mm. Helium was used as a carrier gas. Detection was by a FID detector and integration of peak areas was done with a HP 3396 integrator. The temperature program held an initial temperature of 40° C. for 1.0 minutes then increased at 15 degrees per minute to 280° C., and finally held at a temperature of 280° C. for 5 minutes. To quantify the amount of organic acids extracted by this procedure, a stock solution of 2-bromooctanoate and 2-bromohexadecanoate were added to a sample of undigested Red River crude petroleum oil and then extracted by the same procedure as the bio-digested oil samples. The average area for theses two organic acids was used to estimate the amount of organic acids in micromoles per area unit determined by the GC integrator. The number was calculated to be approximately 1.0 micromoles per 100 area units. The area units for each of the GC peaks are list in Table 2. This number was used to estimate the micromoles organic acids extracted from the oil. This estimate was used to calculate the number of mg of KOH that equaled the number of micromoles of organic acid estimated. This number is listed on the last row in Table 2 as the calculated AN (acid number) for each digestion experiment. These estimated numbers are only based on organic acids that are hydrophobic enough to stay in the oil phase and not move into the aqueous phase. Organic acids measured include the carboxylic acids made by the bacteria and that have been secreted out of the cell and have migrated back to the oil phase. They are also hydrocarbons that are small enough to be extracted into the ethanol aqueous extraction solvent. This number is likely to be less than the total acid number (TAN), a measure often used to evaluate crude petroleum for amenability to alkaline waterflooding.

At the end of the experiment the oil and water were separated and the volume determined. The volume of oil was 11.5 ml for sample without inhibitor, 10.0 ml for the sample with 2-bromooctanoate and 9.0 ml for the sample 2-bromohexadecanoate. The volume of oil for the sample with acrylic acid had increased to 33.5 ml. This indicated that the oil had formed a stable water in oil emulsion at some point during the experiment. This could have lead to a decrease in the amount of oil removed in the 0.31 g removed at day 6 and day 12 for GC analysis. This would have under reported the amount of methyl esters determined by GC analysis. The amount of aqueous phase was determined to be 22.5 ml for the acrylic acid sample and 46 ml, 48 ml and 47.5 ml for the others. This was further evidence that a water in oil emulsion had formed. At the end of the experiment the larger volume of one ml of oil was used to determine the acid number by the alcoholic alkaline extraction of acids and back titration with acid to neutral pH. This was similar to the method used for GC methyl ester formation reported by A. G. Shepherd et al. in Energy Fuels 2010, 24, pp 2300-2311 DOI: 10.1021/ef900949m. The incorporation of aqueous media in the stable emulsion form from the acrylic acid inhibited digestion interfered with the back titration to determine extracted carboxylic acids. The acid number of the emulsion was about twice that of the other oil samples. This was without correcting for the lower concentration of oil in the 1 g of emulsion that was used. The final analysis acid numbers were 10 mg KOH per gram of oil emulsion produced from the acrylic acid inhibited digestion. The calculated acid number for the uninhibited digestion was 5 mg of KOH per gram. The other two inhibited digestions were analyzed to be 4.5 mg for the 2-bromooctanoic acid and 6.5 for the 2-bromohexadecanoic acid inhibited digestion. The undigested oil was determined to have an acid number of 6.5 mg of KOH by analysis of a one gram sample and a 10 gram sample. Ideally this acid analysis should be done on oil samples of 10 to 50 grams for best accuracy.

Results:

The integrator area units of about 20 GC peaks that were seen in each of the digested samples of the Red River petroleum oil are listed in Table 2. The undigested oil sample showed a small level of methyl ester peaks. The earlier eluting peaks are believed to represent methyl ester of lighter hydrocarbon carboxylic acids and the later eluting peaks are believed to represent methyl ester of the heavier organic acids. As a comparison the peak area units are subtotaled for the peaks eluting before 13 minutes compared to the subtotal of the later peaks eluting after 13 minutes. The total of all selected peaks and a total of all the peaks integrated by the GC integrator are listed below each column. The total area units for all the peaks integrated by the GC integrator are listed for the oil samples from Red River oil field in Montana.

Analysis of Results:

The GC analysis of the digestion with the 2-bromohexadecanoate showed a very large peak at 14 minutes, which corresponded to the retention time of the inhibitor compound. There were also some large earlier peaks between 9 and 13 minutes, which made determination of the increase in fatty acids from oil digestion difficult. The quantity of this peak was also higher than the concentration of 2-bromodexadecanoate added as an inhibitor to the aqueous media. It was assumed that the long chain hydrocarbon inhibitor was absorbed into the oil phase at a higher concentration. Therefore, the total peak areas reported for this inhibitor are higher due to the 2-bromohexadecanoate methyl ester. A much smaller peak was seen for the 2-bromooctanoate and did not have much effect on total peak area. No peak was seen for the methyl ester of acrylic acid and it is believed to not be retained at 40° C. on the GC column.

Digestion with the bacteria increases the total amount of carboxylic acids in all the samples. The digestions with the chemical beta-oxidation inhibitors produce about the same or a little more total methyl ester peaks than the bacterial digestion without an inhibitor. A comparison of the subtotal peak area increases for the digestion without inhibitor to the acrylic acid and 2-bromooctanoate inhibited digestions shows a relative difference in the rate of increase. The later eluting peaks increase at a faster rate with the inhibitors than without. For example, the 12 day sample with no inhibitor increase from 5.9 to 45.9 area units for peaks up to 13 minutes. The sample with the acrylic acid inhibitor has an increase of from 5.9 to 43.7 area units, which is less than without inhibitor. The later eluting peaks increase from 3.6 to 14.3 without the inhibitor, but with acrylic acid the later peak areas increase to 22.5 area units. This suggests that the inhibitors are slowing down the conversion of large fatty acids to smaller fatty acids. The optical density measurements and the visual inspection of the samples suggested that the bacteria were growing faster and digesting the oil faster in the uninhibited digestions. After 6 days of digestion the optical density had reached 2.23 for the uninhibited digestion as compared to 0.49 for the acrylic acid inhibited sample and 1.84 for the 2-bromooctanoic acid and 2.4 for the 2-bromohexadeconoic acid. After 12 days of digestion the uninhibited sample had reached 4.0 and the acrylic acid had increased to 1.7 and 2.2 and 2.4 for the other two inhibitors. Therefore, by this experimental analysis one can determine which inhibitors increase the carboxylic acid content or the acid number of the oil fastest with the least amount of oil consumption. The oil consumption can be determined by quantitation of remaining oil or by growth of bacteria were oil is the only carbon source. It appears that all the inhibitors helped reduce the utilization of fatty acids and the consumption of oil while producing an increase in acid number. It also appears that acrylic acid was the most useful because it also helped form a stable water in oil emulsion, which could also improve oil recovery.

TABLE 2

Digestion of oil with and without inhibitors

| Retention Times | No Digestion | No Inhibitor 6 days | AA Inhibitor 6 days | Red River Br C8 Inhibitor 6 days | Br C16 Inhibitor 6 days | No Inhibitor 12 days | AA Inhibitor 12 days | Br C8 Inhibitor 12 days | Br C16 Inhibitor 12 days |
|---|---|---|---|---|---|---|---|---|---|
| 4.2 | | | | | | 0.727 | 0.58 | 0.47 | 0.354 |
| 4.5 | | 0.204 | 0.242 | 0.351 | 0.226 | 1.512 | 1.051 | 0.943 | 0.237 |
| 4.6 | | | | | | 0.374 | 1.519 | | |
| 5.6 | | 1.459 | 0.948 | 0.835 | 1.099 | 3.531 | 2.754 | 1.656 | 0.624 |
| 6.6 | 0.257 | 5.844 | 2.856 | 2.783 | 3.049 | 9.689 | 7.835 | 4.625 | 1.498 |
| 7.6 | 0.251 | 5.304 | 2.724 | 2.476 | 2.553 | 7.075 | 5.761 | 3.349 | 1.246 |
| 8.2 | 0.257 | 0.495 | 0.703 | 0.682 | 0.705 | 0.644 | 0.558 | 0.497 | 0.602 |
| 8.5 | 0.294 | 1.834 | 1.907 | 1.443 | 1.395 | 2.141 | 3.369 | 1.763 | 0.624 |
| 9.4 | 0.418 | 0.725 | 1.575 | 1.146 | 1.131 | 0.531 | 0.747 | 0.681 | 0.476 |
| 10.2 | 0.277 | 0.631 | 1.591 | 1.618 | 1.11 | 0.437 | 0.588 | 0.387 | 0.475 |
| 11 | 0.458 | 1.581 | 2.134 | 2.608 | 4.105 | 1.747 | 1.736 | 0.985 | 1.663 |
| 11.5 | 0.822 | 0.978 | 2.596 | 1.69 | 2.76 | 1.784 | 2.968 | 3.548 | 3.922 |
| 11.7 | 0.411 | 3 | 2.416 | 3.004 | | 3.865 | 3.716 | 2.41 | |
| 12.3 | 0.268 | 1.846 | 1.097 | 1.604 | | 2.597 | 2.722 | 2.973 | 3.095 |
| 12.5 | 2.26 | 5.861 | 4.385 | 4.566 | 4.8 | 8.507 | 6.208 | 5.664 | |
| 12.7 | | 0.636 | | 1.145 | | 0.79 | 1.6421 | 1502 | |
| SubTotal | 5.973 | 30.316 | 25.173 | 25.951 | 22.933 | 45.951 | 43.754 | 31.453 | 14.816 |
| 13 | | 1.261 | 0.521 | 1.421 | | 1.556 | 1.99 | 2.785 | 2.495 |
| 13.1 | | 1.124 | 1.769 | 2.61 | | 1.303 | 2.209 | 4.367 | |
| 13.2 | 1.54 | 2.633 | 3.486 | 3.047 | 1.26 | 2.938 | 4.801 | 7.327 | 3.584 |
| 13.4 | | 1.331 | 1.122 | 2.196 | | 1.805 | 3.72 | 8.161 | 3.088 |
| 13.6 | | 1.383 | 0.783 | 1.314 | 1.997 | 1.811 | 2.005 | 4.176 | 2.779 |
| 13.8 | 1.696 | 2.09 | 2.448 | 3.341 | 3.211 | 1.32 | 2.512 | 4.901 | 4.626 |
| 14 | | 1.297 | 0.447 | 1.661 | | 2.647 | 2.548 | 4.709 | |
| 14.2 | 0.379 | 0.726 | 0.78 | 0.963 | | 0.942 | 2.779 | 1.74 | 0.762 |
| SubTotal | 3.615 | 11.845 | 11.356 | 16.553 | 6.468 | 14.322 | 22.564 | 38.166 | 17.334 |
| Total | 9.588 | 42.161 | 36.529 | 42.504 | 29.401 | 60.273 | 66.318 | 69.619 | 32.15 |
| Total GC | 11.98 | 47.12 | 54.17 | 77.5 | 429.5 | 74.36 | 90.15 | 115.7 | 256.8 |
| For 1 ml conv. To | 38.6 | 152 | 175 | 250 | 1385 | 240 | 291 | 373 | 828 |
| umoles FA | 0.386 | 1.52 | 1.75 | 2.5 | 13.85 | 2.4 | 2.91 | 3.73 | 8.28 |
| Cal. AN | 0.021 | 0.085 | 0.098 | 0.14 | 0.78 | 0.14 | 0.16 | 0.21 | 0.46 |

Example 6

Genetic Engineering of an Alkaline Tolerant Microorganism for Surfactant Production Sand Pack Columns:

Two strains of *Pseudomonas* were used as a host alkaline tolerant bacterium for the introduction of a test group of genes for heterologous expression and biosurfactant production. The production of biosurfactant was in media containing a simple carbon source and was not in contact with petroleum oil. The production of biosurfactant was not linked to short chain hydrocarbon metabolism.

Introduction of rhlAB Rhamnolipid Biosurfactant Production Genes into Alkaliphilic *Pseudomonas akaliphila* and *Pseudomonas toyotomiensis* Strains The rhlAB operon from *Pseudomonas aeruginosa* PAO1 (ATCC BAA-47) encodes genes for the production of a rhamnolipid biosurfactant. It has been demonstrated that heterologous expression of the rhlA and rhlB genes, encoding a rhamnosyl transferase 1 enzyme, is sufficient for production of mono-rhamnolipids with biosurfactant activity in *E. coli* (Ochsner et al 1994; Fang et al DOE report 2007) and *P. putida* (Wittgens 2011).

The rhlA and rhlB genes were introduced into, and heterologously expressed in, alkaliphilic *Pseudomonas* species. The rhlA and rhlB genes were amplified in a single PCR from *Pseudomonas aeruginosa* PAO1 genomic DNA using primers prGFF286 (containing a KpnI restriction site, ribosomal binding site, and the beginning of the rhlA ORF sequence) and prGFF287 (containing a XbaI restriction site, additional stop codon, and end of the rhlB ORF sequence). The resulting fragment was digested with KpnI and XbaI and was subsequently cloned into KpnI/XbaI-digested plasmid pBBR1MCS, placing rhlAB gene expression under control of the LacZ promoter in pBBR1MCS. The resulting plasmid, pGFF88, was sequenced throughout the insert and across the insertion junctions to verify the fidelity of the gene cloning. Plasmids pBBR1MCS and pGFF88 were transformed into *Pseudomonas alcaltphila* (DSM 17744) and *Pseudomonas toyotomiensis* (JCM15604) by electroporation (modified from Sonnenschein et al., 2011 J. Microbiological Methods). Briefly, cells were spread plated onto two Mh-YCA plates (per liter: 25 g NaCl, 15 g agar, 5 g yeast extract, 5 g casamino Acids, 1 g sodium glutamate, 1 g NH4Cl, 1 g KH2PO4, 1 g KCl, 200 mg MgSO4.7H2O, 36 mg FeCl2.4H2O, 0.36 mg MnCl.4H2O, adjusted to pH7.0 with Na2CO3) and grown overnight at 30° C. Cells were scraped into a total volume of 4 mls B3 buffer (300 mM Glucose, 5 mM CaCl2, 25 mM HEPES, 5 mM MgCl2), spun 2 min at 20,000 g, and washed twice with 1 ml ice cold B3 buffer. Cells were then resuspended in 200 µl ice cold B3 buffer. An aliquot of 50 µl cells was mixed with 1 µl pBBR1MCS or pGFF88 DNA, transferred to an electroporation cuvette (2 mm), and pulsed at 2 kV (10 kV/cm) and 900 µl SOC medium were added. The suspension was transferred to a culture tube, incubated 12 hours at 30° C., and spread plated onto Mh-YCA medium containing 400 µl ml chloramphenicol. Plates were incubated at 30° C. Colonies were isolated and checked by PCR, using primers flanking the pBBR1MCS multiple cloning site and primers internal to the rhlAB sequence. Additionally, rDNA sequences were PCR amplified and sequenced, confirming that the isolates were the appropriate *Pseudomonas* species.

Production of rhamnolipid biosurfactant was tested in engineered strains using the oil spreading assay (Fang et al DOE report 2007). Cells were grown three days at 30° C. in YCA-10 medium (per liter: 25 g NaCl, 5 g yeast extract, 5 g casamino Acids, 5 g Na2CO3, 1 g sodium glutamate, 1 g NH4Cl, 1 g KH2PO4, 1 g KCl, 200 mg MgSO4.7H$_2$O, 36 mg FeCl2.4H2O, 0.36 mg MnCl.4H2O, adjusted to pH10.0 with KOH) containing 5 µg/ml chloramphenicol. For oil spreading assays, 50 mls of distilled water was dispensed into a 15 cm petri dish and 50 µl of petroleum oil was added to the surface of the water. A 10 µl drop of medium or culture suspension was added to the surface of the oil, and the diameter of the clear zone (if any) was measured after 2 minutes. Results are shown below in Table 3.

TABLE 3

| Sample | Description | Clear zone diameter (mm) |
|---|---|---|
| Medium Mh-YCA (pH7) | | <1 |
| Medium YCA, pH10 | | <1 |
| Surfactin (purified)--100 µg/ml | | 13 |
| GFF255 | *P. alcaliphila* + pBBR1MCS | 1 |
| GFF253 | *P. alcaliphila* + pGFF88 | 29 |
| GFF257 | *P. toyotomiensis* + pBBR1MCS | 2 |
| GFF261 | *P. toyotomiensis* + pGFF88 | 30 |

Production of rhamnolipid was tested in culture supernatants of six day old cultures in the resulting *P. alcaliphila* strain harboring the rhlAB vector (GFF 253) using the orcinol assay (as described in Fang et al DOE report 2007). Results were compared to assay standards made from purified rhamnolipid (Sigma-Aldrich), which indicated that the strain produced between 50 mg/L and 100 mg/L rhamnolipid.

Sand Pack Columns:

To test the ability of the rhamnolipid biosurfactant producing engineered strains, a six day old culture was tested for its ability to elute oil from a small sand pack column. One small sand pack column was about 50 ml in volume and was made by filling water containing glass column with dry 30 mesh sand. The pore volume was determined by measuring the empty weight of the column, the dry weight of the sand needed to fill the column and the final weight of the water filled sand column. Two columns were prepared this way, with column #1 having a pore volume of 21.5 ml and the other column #2 having a pore volume of 22.8 ml. Each column was filled with oil by pumping oil into the bottom of the vertical columns. The petroleum used in this experiment was moderately heavy (API 24) petroleum from Ecuador. The amount of oil pumped into the columns was determined by weight to be 15.4 g for column #1 and 15.0 g for column #2. At a density of 0.91 the oil filled 16.9 ml of the 21.5 ml pore volume in column #1 (79%) and 16.5 ml of the 22.8 ml pore volume in column #2 (72.4%).

The oil was then eluted off with water at a flow rate of about 6 mL/minute. After about 30 pore volumes of water the weight of the oil eluted was determined. The amount of oil eluted from column #1 was 10.57 g or 68.6% of the oil that was applied. The amount of oil eluted from column #2 was 8.73 g or 58.2% of the oil that was applied. Next, a pH 10.0 buffer was pumped into each column for another 30 pore volumes to determine if more oil could be eluted with a higher pH buffer. The additional weight of the oil eluted by the 30 pore volumes was 0.38 g from column #1 and 0.23 g from column #2. Next a 50 ml aliquot of each culture was pumped through each column at the same flow rate for two hours which was approximately 30 pore volumes of fluid flow. The rhamnolipid biosurfactant-producing *P. alcaliphila* strain, harboring the rhlAB vector (GFF 253) was applied to column #1. The *P. alcaliphila* strain harboring an empty vector without the rhlA and rhlB genes (GFF 255) was applied to column #2. The amount of oil recovered from biosurfactant producing strain was an additional 0.57 g and the amount produced from the empty vector control (GFF 255) was 0.25 g. An additional two days of flow of each microbe containing solutions eluted another 0.32 g from column #1 and an additional 0.61 g from column #2. At the end of the experiment, each column was extracted with a mixture on hexane and toluene. The extracted mixture was dried with the flow of warm air (about 50° C.) for several days to remove the hexane and toluene. The weight of each sample was used to determine the mass of each column. The total weight of solvent extracted oil was 2.65 g or 17.2% of the original oil applied to column #1 and 3.31 g or 22.1% from column #2. The total oil recovered from column #1 was 11.84 g or 76.9% by aqueous elution and 14.49 g or 94.1% of the oil applied by total extraction. The total oil recovered from column #2 was 9.82 g or 65.5% by aqueous elution and 13.13 g or 87.5% of the oil applied by total extraction.

The amount of oil eluted immediately following the application of surfactant-producing microbes was greater than in the application on the microbes with the empty vector, which did not exhibit the presence of surfactant in the oil spreading assay. However, during the subsequent two days of elution after the initial application of microbes, slightly more oil was eluted with the empty vector control (GFF255 versus GFF253). The amount of oil eluted by the rhamnolipid was fairly small and may have been limited by the low level production (50 to 100 mg/l) or by the fact that rhamnolipid has lower activity at a high pH and is better suited for a neutral or slightly acidic pH. To evaluate the pH effect, a larger sand pack column with a volume of 250 ml was run at pH 7.

The larger column was packed the same way as the smaller column and had 422.5 g of sand with a water pore volume of 101.1 ml in column #1 and 427.1 g of sand and a water pore volume of 100.8 ml in column #2. Each column was filled with oil by pumping from the bottom until oil started to elute from the top. A total of 88 g of oil was pumped onto column #1 and 83.5 g to column #2. The oil was left on the column for two days before applying the media buffer solutions. For the lager columns the flow rate was reduced to 1.0 ml/minute and each 50 ml eluted for the first two pore volumes (200 ml) was collected. The amount of oil was determined by removing the water from each collection tube and weighing the remaining oil. The fluid used in both columns was the pH 7 media that the microbes were grown in. The next 500 ml, or 5 pore volumes, were collected as 100 ml samples and the weight of the oil determined the same way. At the end of pore volume number 7, each of the two different bacterial cultures was applied to one of the two columns. The cells producing rhamnolipid (GFF253) were applied to column #1 and the empty vector control cells (GFF255) were applied to column #2. The next two pore volumes were collected as 50 ml samples, and the weight of oil eluted was determined by removing the water as before. The next four pore volumes were eluted in two collections of two pore volumes each. The amount of oil in each sample was determined and is listed in Table 4 below. At the end of the aqueous elution experiment, the columns were dried with air flow and then extracted with 100 ml of toluene. The toluene was dried with the flow of warm air until all the volatile solvent was removed. The final weight of the toluene extract after a few days' drying indicated the amount of unrecovered oil remaining on the columns after the bacterial extractions.

The results of the neutral pH column were similar to the smaller high pH column. The bacteria producing the rhamnolipid eluted more oil in the first pore volume following the injection of cells. The control microbes (GFF255), containing an empty vector without genes coding for the production of rhamnolipid, appeared to have had a delayed affect on oil elution. This may have been due to the higher cell density of GFF255 compared to the GFF253 strain (4.25 optical density at 600 nm vs. 2.48 for the GFF253 strain).

The amount of oil actually eluted as a result of the rhamnolipid was small. While the gene was successfully transferred into this alkaline tolerant strain, as shown above, the amount of oil elution was small. This may be due to low expression levels or the ineffectiveness of this particular biosurfactant at high pH. However, this is a useful way to measure the benefit of various biosurfactants for oil recovery.

TABLE 4

| Pore volumes eluted | Col. # 1 Total g of oil recovered | Col. #2 Total g of oil recovered | Col. #1 % of oil recovered | Col. # 2 % of oil recovered |
|---|---|---|---|---|
| 0.5 | 43.86 | 43.12 | 49.8 | 51.6 |
| 1.0 | 49.06 | 49 | 55.75 | 58.7 |
| 1.5 | 52.3 | 51.9 | 59.4 | 62.2 |
| 2 | 54.5 | 54.1 | 61.9 | 64.8 |
| 3 | 58.6 | 57.5 | 66.6 | 68.9 |
| 4 | 61.3 | 60.1 | 69.6 | 72 |
| 5 | 63.3 | 64.2 | 71.9 | 76.9 |
| 6 | 64.7 | 65.8 | 73.5 | 78.8 |
| 7 | 65.5 | 66.8 | 74.4 | 80 |
| 7.5 Add Cells | 65.9 | 67.2 | 74.9 | 80.5 |
| 8 | 67 | 67.5 | 76.1 | 80.8 |
| 8.5 | 70 | 68.1 | 79.5 | 81.6 |
| 9 | 70.6 | 69.5 | 80.2 | 83.2 |
| 11 | 71 | 71.7 | 80.7 | 85.9 |
| 13 | 71.2 | 74 | 80.9 | 88.6 |
| Toluene Extract | 12 | 9.9 | 13.6 | 11.8 |

Example 7

The Introduction of Other Biosurfactant Production Pathways into Other Alkaline Tolerant Microbes Introduction of Rhamnolipid Biosurfactant Production Genes into Alkalitolerant *Bacillus halodurans*

The rhlA and rhlB were introduced into *Bacillus halodurans* strain C-125 (JCM9153), an alkalitolerant strain that grows under high pH conditions of over pH11. The rhlA and rhlB genes were amplified in a single PCR from *Pseudomonas aeruginosa* PAOJ genomic DNA using primers prGFF296 (containing the beginning of the rhlA ORF) and prGFF300 (containing a SacI restriction site, an additional stop codon, and the end of the rhlB ORF sequence). A DNA fragment containing a SalI restriction site, the hag (sigmaD) promoter, and the beginning of the rhlA gene was generated by PCR from *B. halodurans* genomic DNA using primers prGFF294 (containing a SalI restriction site and sequence upstream of the hag ORF) and prGFF295 (containing reverse complement sequence to the beginning of the rhlA ORF followed by reverse complement sequence to hag promoter sequence immediately upstream of the hag ORF). In a subsequent PCR, the two fragments were joined and amplified as a single fragment, using primers prGFF294 and prGFF300. The resulting fragment was digested with SalI and SacI and was subsequently cloned into SalI/SacI-digested plasmid pNW33N. The resulting plasmid, pGFF94, was sequenced throughout the insert and across the insertion junctions to verify the fidelity of the gene cloning. Plasmids pNW33N and pGFF94 were transformed into *B. halodurans* JCM9153 and plated on succinate nutrient agar medium containing 3 μg/mlchloramphenicol as described previously (Wallace 2011). Colonies were isolated. PCR confirmed the presence of the plasmid in isolates, using primers flanking the pNW33N multiple cloning site and primers internal to the rhlAB sequence.

Introduction of Surfactin Biosurfactant Production Genes into Alkalitolerant *Bacillus halodurans*

In one example, a DNA segment containing the operon for surfactin production, including srfAA, srfAB, comS, srfAC, srfAD, ycxA, ycxB, ycxC, ycxD, and sfp from *Bacillus subtilis* strain ATCC21332, are introduced into *Bacillus halodurans* strain C-125 (JCM9153), an alkalitolerant strain that grows under high pH conditions of over pH11. The DNA segment is amplified in a single PCR from *Bacillus subtilis* strain ATCC21332 genomic DNA using primers prGFF314 (containing an SbfI restriction site and sequence upstream of the srfAA ORF) and prGFF315 (containing a SwaI blunt restriction site sequence downstream of sfp ORF sequence). The resulting fragment is digested with SbfI and SwaI and subsequently cloned into SbfI/SmaI-digested plasmid pNW33N. The resulting plasmid is introduced into *Bacillus halodurans* strain C-125 (JCM9153) by established methods. Alternatively, a DNA segment containing the same genes are introduced into *Bacillus halodurans* strain C-125 (JCM9153) under the regulation of a different promoter for optimal expression in *Bacillus halodurans*. For example, the promoter upstream of the hag gene from *Bacillus halodurans* strain C-125 (JCM9153) is amplified by PCR using primers prGFF313 (containing a hindIII restriction site followed by sequence matched to the 5 prime end of the promoter) and prGFF312 (containing a SbfI restriction site followed by reverse complement sequence matched to the hag promoter immediately upstream of the ribosomal binding site). The resulting fragment is cut and ligated into pNW33N at the HindIII and SbfI sites. A DNA segment containing the operon for surfactin production, including srfAA, srfAB, comS, srfAC, srfAD, ycxA, ycxB, ycxC, ycxD, and sfp from *Bacillus subtilis* strain ATCC21332, is PCR amplified using prGFF311 (containing an SbfI restriction site, a ribosomal binding site, and sequence matched to the beginning of the srfAA ORF) and prGFF315 (containing a SwaI blunt restriction site sequence downstream of sfp ORF sequence). The resulting segment is cut with SbfI and SwaI and cloned into the SbfI and SmaI sites in the pNW33N vector containing the hag promoter, placing the surfactin operon under the regulation of the hag promoter. The resulting plasmid is introduced into *Bacillus halodurans* strain C-125 (JCM9153) by established methods.

TABLE 5

| Primer name | Sequence | Notes |
|---|---|---|
| prGFF286 | CCTTGGAggtaccAGGAGGTTTTTATTAtgcggcgcgaaagtctgttgg<br>(SEQ ID NO: 11) | forward oligo for RhlAB amplification for pBBR1MCS vectors (KpnI site plus RBS plus other plus beginning of RhlAB) |
| prGFF287 | aaccaaggTCTAGAtcaTTAtcaggacgcagccttcagccatcg<br>(SEQ ID NO: 12) | reverse oligo for RhlAB amplification for pBBR1MCS vectors (XbaI site plus stop codon plus end of RhlAB) |
| prGFF294 | ccttggaGTCGACctcgcgttacgctctttctgt<br>(SEQ ID NO: 13) | extra sequence plus SalI plus hag promoter forward |
| prGFF295 | ggcccttgcaaaccgataccaacagacttcgcgccgcatTAAAATTTCCTCCTTGAAATGTGTT<br>(SEQ ID NO: 14) | Beginning of RhlAB (rc) plus hag promoter sequence immediately before start (rc) |
| prGFF296 | ATGCGGCGCGAAAGTCTGTTGGTATC<br>(SEQ ID NO: 15) | start of RhlAB |
| prGFF300 | CGAgagctcAAGTAACGGTTGAGCGAAAAATAAAAAAGACCTGGAATAAATCCAGATCTTTAAATGGAAGCAAAttaTCAGGACGCAGCCTTCAGCCATC<br>(SEQ ID NO: 16) | SacI site plus sequence after hag (rc) plus extra stop plus end of RhlAB (rc) |
| prGFF311 | AAAGACAAcctgcaggCGGAAAACACATTTCAAGGAGGAAATTTTAatggaaataacttttttaccctttaacggatgcacaa<br>(SEQ ID NO: 17) | Random sequence plus SbfI restriction site plus 30 nt immediately upstream of hag c-125 ORF plus first 36 nt in srfAA ORF |
| prGFF312 | AACGTTTAcctgcaggCTTGTGGTTGGTGTAAACTTAATCC<br>(SEQ ID NO: 18) | Random sequence plus SbfI site plus sequence upstream of c-125 hag shine dalgarno site (rc) |
| prGFF313 | ccttggaAAGCTTctcgcgttacgctctttctgt<br>(SEQ ID NO: 19) | Random sequence plus HinDIII plus hag promoter forward |
| prGFF314 | aaagacaaCCTGCAGGagttacttggaggatactgtgaggagagacaatcag<br>(SEQ ID NO: 20) | Forward primer for amplification of srfA operon; random sequence plus SbfI restriction site plus sequence upstream of srfA1 ORF |
| prGFF315 | cgatccatATTTAAATaaaattggggcctcctgaatatggtgctcattggtg<br>(SEQ ID NO: 21) | Reverse primer for amplification of srfA operon; random sequence plus SwaI restriction site plus sequence downstream of sfp; note that sequence differs between genbank sequences at prGFF315 |

The invention claimed is:

1. A method of enhancing oil recovery comprising
   (a) water-flooding an oil reservoir with an alkaline fluid or a fluid containing a compound toxic to indigenous microbes to reduce the concentration of microbes that have the ability to utilize short chain hydrocarbons of about 12 carbons or less,
   (b) inoculating said oil reservoir with a consortium comprising microbes that naturally are, or are engineered to be, obligatory alkaliphilic, halo-alkaliphilic or alkaline tolerant and naturally are, or are engineered to be, deficient in their ability to utilize short chain hydrocarbons of 12 carbons or less but have the ability to convert hydrocarbons into fatty acids,
   (c) allowing the consortium to proliferate and degrade hydrocarbons of greater than 12 carbons, and
   (d) obtaining enhanced oil recovery from the oil reservoir, wherein step (c) is performed under alkaline conditions.

2. The method of claim 1, wherein said consortium comprises microbes that are naturally alkaliphilic, halo-alkaliphilic or alkaline tolerant.

3. The method of claim 1, wherein said consortium comprises microbes that are engineered to be alkaliphilic, halo-alkaliphilic or alkaline tolerant.

4. The method of claim 1, 2, or 3, wherein said consortium comprises microbes that are naturally deficient in their ability to degrade short chain hydrocarbons of 12 carbons or less.

5. The method of claim 1, 2, or 3, wherein said consortium comprises microbes that are engineered to be unable to degrade short chain hydrocarbons of 12 carbons or less.

6. The method of claim 5, wherein said consortium comprises microbes in which one or more metabolic pathways for degrading short chain hydrocarbons of 12 carbons or less are down regulated or deleted or modified.

7. The method of claim 1, wherein said consortium comprises microbes in which one or more metabolic pathways for degrading hydrocarbon chains of greater than 12 carbons are introduced.

8. The method of claim 1, wherein said consortium comprises microbes that are capable of utilizing hydrocarbons having at least 40 carbons present in the oil reservoir as a carbon source.

9. The method of claim 1, wherein said consortium comprises microbes that are additionally capable of growing in an environment of a salt concentration of at least about 5%.

10. The method of claim 9 wherein a salt concentration of at least about 5% is provided in the reservoir.

11. The method of claim 1, wherein said consortium comprises microbes that are capable of utilizing carbons selected from the group consisting of glucose, sucrose, mannose, starch, glycerin, and organic acids.

12. The method of claim 1, 8, 9, 10, or 11, wherein in step b a nutrient mixture comprising a soluble carbon source is injected into said oil reservoir along with said consortium.

13. The method of claim 12, wherein said nutrient mixture further comprises at least one non-hydrocarbon nutrient.

14. The method of claim 13, wherein said non-hydrocarbon nutrient is selected from the group consisting of yeast extract, peptone, succinate, lactate, formate, acetate, propionate, glutamate, glycine, lysine, citrate, glucose, and vitamin solutions.

15. The method of claim 1, wherein said microbes are selected from the domain Archaea and bacteria.

16. The method of claim 1, wherein the consortium is able to grow at pH of 9.0 or higher.

17. The method of claim 1, wherein the consortium is able to grow at pH of 10.0 or higher.

18. The method of claim 1, wherein said consortium comprises microbes selected from the domain Archaea and bacteria that are obligatory alkaliphiles, halo-alkaliphiles or alkaline tolerant, and have the ability to utilize ring aromatic hydrocarbons.

19. The method of claim 1, wherein said consortium comprises microbes selected from the domain Archaea and bacteria that are obligatory alkaliphiles, halo-alkaliphiles or alkaline tolerant, that have the ability to utilize modified hydrocarbons containing sulfur.

20. The method of claim 1, wherein said consortium comprises microbes selected from the domain Archaea and bacteria that are obligatory alkaliphiles, halo-alkaliphiles or alkaline tolerant, and have the ability to utilize modified hydrocarbons containing nitrogen.

21. The method of claim 1, wherein said consortium comprises microbes selected from the domain Archaea and bacteria that are obligatory alkaliphiles, halo-alkaliphiles or alkaline tolerant, and have the ability to produce surfactants.

22. The method of claim 1, wherein said consortium comprises microbes selected from the domain Archaea and bacteria that are obligatory alkaliphiles, halo-alkaliphiles or alkaline tolerant, and have the ability to produce extracellular polymers.

23. The method of claim 1, further comprising the step of adding to the reservoir at least one chemical inhibitor to control a metabolic pathway of at least one indigenous microbe present in the reservoir or obligatory alkaliphilic, halo-alkaliphilic or alkaline tolerant microbe inoculated into the reservoir.

24. The method of claim 23 wherein said chemical inhibitor inhibits the degradation of short-chain alkanes of 1 to 4 carbon atoms by said indigenous or inoculated microbe.

25. The method of claim 1, wherein said consortium comprises microbes selected from the domain Archaea and bacteria that are obligatory alkaliphiles, halo-alkaliphiles or alkaline tolerant, and that have been engineered to produce surfactant.

26. The method of claim 25, wherein the production of surfactant is independent of the expression of genes that code for the degradation of hydrocarbons.

* * * * *